US009011754B2

(12) United States Patent
Leong et al.

(10) Patent No.: US 9,011,754 B2
(45) Date of Patent: *Apr. 21, 2015

(54) MANUFACTURING THREE-DIMENSIONAL SCAFFOLDS USING ELECTROSPINNING AT LOW TEMPERATURES

(75) Inventors: Meng Fatt Leong, Singapore (SG); Tze Chiun Lim, Singapore (SG); Kerm Sin Chian, Singapore (SG)

(73) Assignee: Nanyang Technological University, Singapore (SG)

( * ) Notice: Subject to any disclaimer, the term of this patent is extended or adjusted under 35 U.S.C. 154(b) by 795 days.

This patent is subject to a terminal disclaimer.

(21) Appl. No.: 12/517,701

(22) PCT Filed: Dec. 5, 2007

(86) PCT No.: PCT/SG2007/000413
§ 371 (c)(1),
(2), (4) Date: Nov. 16, 2009

(87) PCT Pub. No.: WO2008/069759
PCT Pub. Date: Jun. 12, 2008

(65) Prior Publication Data
US 2010/0093093 A1 Apr. 15, 2010

Related U.S. Application Data

(60) Provisional application No. 60/872,800, filed on Dec. 5, 2006.

(51) Int. Cl.
B29C 47/00 (2006.01)
A61L 27/60 (2006.01)
A61L 27/38 (2006.01)
A61L 27/56 (2006.01)
A61L 27/58 (2006.01)
D01D 5/00 (2006.01)
C12N 5/00 (2006.01)

(52) U.S. Cl.
CPC ............. *A61L 27/60* (2013.01); *A61L 27/3847* (2013.01); *A61L 27/56* (2013.01); *A61L 27/58* (2013.01); *D01D 5/0076* (2013.01)

(58) Field of Classification Search
None
See application file for complete search history.

(56) References Cited

U.S. PATENT DOCUMENTS

| 6,103,255 | A | 8/2000 | Levene et al. | |
|---|---|---|---|---|
| 6,231,879 | B1 | 5/2001 | Li et al. | |
| 6,899,873 | B2 | 5/2005 | Ma et al. | |
| 7,083,854 | B1* | 8/2006 | Joo et al. ................ | 428/372 |
| 2002/0090725 | A1* | 7/2002 | Simpson et al. ............. | 435/402 |
| 2003/0021827 | A1 | 1/2003 | Malaviya et al. | |
| 2003/0059460 | A1 | 3/2003 | Tabata | |
| 2004/0005297 | A1 | 1/2004 | Connelly et al. | |
| 2004/0018226 | A1* | 1/2004 | Wnek et al. ................ | 424/443 |
| 2005/0073075 | A1* | 4/2005 | Chu et al. ................ | 264/465 |
| 2006/0019362 | A1 | 1/2006 | Yu et al. | |
| 2006/0199876 | A1 | 9/2006 | Troczynski | |
| 2006/0263417 | A1* | 11/2006 | Lelkes et al. ............. | 424/443 |

FOREIGN PATENT DOCUMENTS

| WO | WO 01/02033 | 1/2001 |
|---|---|---|
| WO | WO 02/062968 | 8/2002 |
| WO | WO 03/007790 | 1/2003 |
| WO | WO 03/099230 | 1/2003 |
| WO | WO 04/000915 | 12/2003 |
| WO | WO 2006/099332 | 9/2006 |
| WO | WO 2007/029913 | 3/2007 |
| WO | WO 2007/056418 | 5/2007 |
| WO | WO 2008/069760 | 6/2008 |
| WO | WO 2008/069761 | 6/2008 |

OTHER PUBLICATIONS

Nair et al. Development of novel tissue engineering scaffolds via electrospinning. Expert Opinion on Biological Therapy, vol. 4, No. 5, pp. 659-668, 2004.*
McCann et al. Highly porous fibers by electrospinning into a cryogenic liquid. Journal of the American Chemical Society, vol. 128, pp. 1436-1437, Jan. 13, 2006.*
Simonet et al. Ultraporous 3D polymer meshes by low-temperature electrospinning: Use of ice crystals as a removable void template. Polymer Engineering and Science, vol. 47, No. 12, pp. 2020-2026, Nov. 1, 2007.*
U.S. Appl. No. 12/517,891, filed Jun. 5, 2009, Chian, et al.
U.S. Appl. No. 12/517,941, filed Jun. 5, 2009, Chian, et al.
Abstracts of Papers Database accession No. (2007:886977), Aug. 15, 2007. Zhang et al. Preparation of aligned porous biodegradable polymers by directional freezing.
Albes, et al., "Biophysical properties of the gelatin-resorcin-formaldehyde/glutaraldehyde adhesive.", *The Annals of Thoracic Surgery*, 56(4): 910-915 (1993).
Ang, et al., "Fabrication of 3D chitosan-hydroxyapatite scaffolds using a robotic dispensing system", *Materials Science and Engineering C*, 20(1):35-42 (2002).
Bartold, et al., "Principles and applications of cell delivery systems for periodontal regeneration.", *Periodontology*, 41:123-135 (2006).
Beckstead, et al., "Esophageal epithelial cell interaction with synthetic and natural scaffolds for tissue engineering", *Biomaterials*, 26(31):6217-6228 (2005).
Brannon-Peppas, "Polymers in Controlled Drug Delivery", *Medical Plastics and Biomaterials* (1997).
Brauker, et al., "Neovascularization of synthetic membranes directed by membrane microarchitecture.", *Journal of Biomedical Materials Research*, 29(12):1517-1524 (1995).
Chen, et al., "Development of biodegradable porous scaffolds for tissue engineering", *Materials Science and Engineering*, C17(1-2):63-69 (2001).
Chupa, et al., "Vascular cell responses to polysaccharide materials: in vitro and in vivo evaluations.", *Biomaterials*, 21(22):2315-2322 (2000).

(Continued)

Primary Examiner — Jennifer Dunston
(74) Attorney, Agent, or Firm — Pabst Patent Group LLP

(57) ABSTRACT

The present invention refers to an apparatus and a method for the manufacture of a three-dimensional scaffold at low temperatures and the respective use of this method and apparatus.

7 Claims, 11 Drawing Sheets

(56) References Cited

OTHER PUBLICATIONS

Clark, et al., "Tissue Engineering for Cutaneous wounds", *Journal of Investigative Dermatology*, 127(5):1018-1029 (2007).
Dalton, et al., "Biophysical properties of the gelatin-resorcin-formaldehyde/glutaraldehyde adhesive.", *Biomacromolecules*, 7(3):686-690 (2006).
Demir, et al., "Electrospinning of polyurethane", *Polymer*, 43:3303-3309 (2002).
Deng, et al., "Poly(L-lactic acid)/hydroxyapatite hybrid nanofibrous scaffolds prepared by electrospinning", *Journal of Biomaterials Science*, 18(1):177-130 (2007).
Deng, et al., "Study on biodegradable polymer. 3. Synthesis and characterization of poly(DL-lactic acid)-co-poly(ethylene glycol)-co-poly(L-lysine) copolymer", *European Polymer Journal*, 38(7):1435-1441 (2002).
Deville, et al., "Freezing as a path to build complex composites", *Science*, 311(5760):515-518 (2006).
Duan, et al., "Hybrid nanofibrous membranes of PLGA/chitosan fabricated via an electrospinning array", *Journal of Biomedical Materials Research, Part A*, 83(3): 868-878 (2007).
Dupont-Gillain and Rouxhet, "Modulable nanometer-scale surface architecture using spin-coating on an adsorbed collagen layer.", *Nano Letters*, 1(5):245-251 (2001).
Endres, et al., "Osteogenic induction of human bone marrow-derived mesenchymal progenitor cells in novel synthetic polymer-hydrogel matrices.", *Tissue Engineering*, 9(4):689-702 (2003).
Ferguson, et al., "Scar-free healing: from embryonic mechanisms to adult therapeutic intervention.", *Philos Trans R Soc Lond B Biol Sci.*, 359(1445):839-850 (2004).
Gilbert, et al., "Decellularization of tissues and organs.", *Biomaterials*, 27(19):3675-3683 (2006).
Griffith, "Emerging design principles in biomaterials and scaffolds for tissue engineering.", *Ann. N.Y. Acad. Sci.*, 961:83-95 (2002).
Han and Gouma, "Electrospun bioscaffolds that mimic the topology of extracellular matrix.", *Nanomedicine: Nanotechnology, Biology and Medicine*, 2(1):37-41 (2006).
Harris and Cooper, L.F., "Comparison of bone graft matrices for human mesenchymal stem cell-directed osteogenesis.", *J Biomed Mater Res A.*, 68(4):747-755 (2004).
Hood, et al., "Perioperative Autologous Sequestration III: A new Physiologic Glue with Wound Healing Properties", *Proceedings of the American Academy of cardiovascular perfusion*, 14:126-129 (1993).
Huang, et al., "A review on polymer nanofibers by electrospinning and their applications in nanocomposites", *Composites Science and Technology*, 63(15):2223-2253 (2003).
Huang, et al., "Electrospraying of a nano-hydroxyapatite suspension", *Journal of Materials Sciences*, 39(3):1029-1032 (2004).
Jain, et al., "Engineering vascularized tissue.", *Nature Biotechnology*, 23(7):821-823 (2005).
Jansen, et al., "Surgical mesh as a scaffold for tissue regeneration in the esophagus.", *European Surgical Research*, 36(2):104-111 (2004).
Jeong, et al., "Tissue-engineered vascular grafts composed of marine collagen and PLGA fibers using pulsatile perfusion bioreactors.", *Biomaterials*, 28(6):1115-1122 (2007).
Kaplan, et al., "Electrospinning *Bombyx mori* silk with poly(ethylene oxide).", *Biomacromolecules*, 3(6):1233-1239 (2002).
Kim, et al., "Control of degradation rate and hydrophilicity in electrospun non-woven poly(D,L-lactide) nanofiber scaffolds for biomedical applications.", *Biomaterials*, 24(27):4977-4985 (2003).
Klawitter, et al., "An evaluation of bone growth into porous high density polyethylene.", *J Biomed Mater Res*, 10(2):311-323 (1976).
Lannutti, et al., "Electrospinning for tissue engineering scaffolds", *Materials Science and Engineering C*, 27:504-509 (2007).
Larrondo, et al, "Electrostatic Fiber Spinning from Polymer Melts. III.Electrostatic Deformation of a Pendant Drop of Polymer Melt", *Journal of Polymer Science: Polymer Physics Edition*, 19( ):933-940 (1981).

Lee, et al, "Frost formation on a vertical plate in simultaneously developing flow", *Experimental Thermal and Fluid Science*, 26:939-945 (2002).
Levenberg, et al., "Engineering vascularized skeletal muscle tissue.", *Nature Biotechnology*, 23(7):879-884 (2005).
Lheureux, et al., *Journal of Vascular Surgery*, 17:499-509 (1993).
Li and Xia, "Electrospinning of nanofibers: Reinventing the wheel?", *Advanced Materials*, 16:1151-1170 (2004).
Li, et al, "Electrospun nanofibrous structure: A novel scaffold for tissue engineering", *J Biomed Mater Res*, 60(4):613-621 (2002).
Li, et al., "Effects of filtration seeding on cell density, spatial distribution, and proliferation in nonwoven fibrous matrices.", *Biotechnology Progress*, 17(5):935-944 (2001).
Li, et al., "Low-molecular-weight peptides derived from extracellular matrix as chemoattractants for primary endothelial cells.", *Endothelium*, 11(3-4):199-206 (2004).
Libbrecht, "The physics of snow crystals", *Reports on Progress in Physics*, 68(4):855-895 (2005).
Lindberg and Badylak, "Porcine small intestinal submucosa (SIS): a bioscaffold supporting in vitro primary human epidermal cell differentiation and synthesis of basement membrane proteins.", *Burns*, 27(3):254-266 (2001).
Liu, et al., "Experimental study on the ice pattern fabrication for the investment casting by rapid freeze prototyping (RFP)", *Computers in Industry*, 48(3):181-197 (2002).
Liu, et al., "Ordered porous ZnO thin films formed by dip-coating method using PS templates", *Journal of Sol-Gel Science and Technology*, 40(1):25-30 (2006).
Liu, et al., "Porous morphology, porosity, mechanical properties of poly(alpha-hydroxy acid)-tricalcium phosphate composite scaffolds fabricated by low-temperature deposition", *Journal of Biomedical Material Research Part A*, 82(3):618-629 (2007).
Ma, "Scaffolds for tissue fabrication.", *Materials Today*, 7(5):30-40 (2004).
MacNeil, "Progress and opportunities for tissue-engineered skin", *Nature*, 445(7130):874-880 (2007).
Mao, et al., "Structure and properties of bilayer chitosan-gelatin scaffolds", *Biomaterials*, 24(6):1067-1074 (2003).
Marshall, et al., *Abstracts of Papers of the American Chemical Society*, 228:U386-U386 (2004).
Megelski, et al., "Micro- and Nanostructured Surface Morphology on Electrospun Polymer Fibers", *Macromolecules*, 35(22):8456-8466 (2002).
Meyer, et al., "Extracellular matrix proteins in the porcine pancreas: a structural analysis for directed pancreatic islet isolation.", *Transplant Proc.*, 30(2):354 (1998).
Mo, et al., "Electrospun P(LLA-CL) nanofiber: a biomimetic extracellular matrix for smooth muscle cell and endothelial cell proliferation", *Biomaterials*, 25(10):1883-1890 (2004).
Moran, et al., "Characterization of polylactic acid-polyglycolic acid composites for cartilage tissue engineering.", *Tissue Engineering*, 9(1):63-70 (2003).
Oh, et al., "In vitro and in vivo characteristics of PCL scaffolds with pore size gradient fabricated by a centrifugation method", *Biomaterials*, 28(9):1664-1671 (2007).
Pham, et al., "Electrospinning of polymeric nanofibers for tissue engineering applications: a review.", *Tissue Engineering*, 12(5):1197-1211 (2006).
Robinson, et al., "Myocardial tissue replacement with extracellular matrix scaffolds", *J Am Coll Cardiol*, 41(6):514 (2003).
Schenke-Layland, et al., "Impact of decellularization of xenogeneic tissue on extracellular matrix integrity for tissue engineering of heart valves.", *J Struct Biol*, 143(3):201-208 (2003).
Schindler, et al., "A synthetic nanofibrillar matrix promotes in vivo-like organization and morphogenesis for cells in culture.", *Biomaterials*, 26(28):5624-5631 (2005).
Smith and Ma, "Nano-fibrous scaffolds for tissue engineering", *Colloids and Surfaces B: Biointerfaces*, 39:125-131 (2004).
Smith and Stolle, "Nonisothermal two-dimensional film casting of a viscous polymer", *Polym. Eng. Sci.*, 40(8):1870-1877 (2000).
Stankus, et al., "Microintegrating smooth muscle cells into a biodegradable, elastomeric fiber matrix.", *Biomaterials*, 27(5):735-744 (2006).

(56) References Cited

OTHER PUBLICATIONS

Subbiah, et al., "Electrospinning of nanofibers", *Journal of Applied Polymer Science*, 96(2):557-569 (2005).
Sun, et al., "Frost formation on a vertical plate in simultaneously developing flow", *Applied Physics Letters*, 86(11):113504 (2005).
Sunderkötter, et al., "Macrophage-derived angiogenesis factors.", *Pharmacology & Therapeutics*, 51(2):195-216 (1991).
Sutherland, et al., "Regeneration of bladder urothelium, smooth muscle, blood vessels and nerves into an acellular tissue matrix.", *J Urol*, 156(2 pt 2):571-577 (1996).
Thorn, et al., "Autologous fibrin glue with growth factors in reconstructive maxillofacial surgery.", *J Oral Maxillofac. Surg*, 33(1):95-100 (2004).
Valentin, et al., "Extracellular matrix bioscaffolds for orthopaedic applications. A comparative histologic study.", *J Bone Joint Surg Am*, 88(12):2673-2686 (2006).
Wu, et al., "Preparation and assessment of glutaraldehyde-crosslinked collagen-chitosan hydrogels for adipose tissue engineering.", *Journal of Biomedical Materials Research Part A*, 81A(1):59-65 (2007).
Yan, et al., "Layered manufacturing of tissue engineering scaffolds via multi-nozzle deposition", *Material Letters*, 57(18):2623-2628 (2003).
Yang, "The design of scaffolds for use in tissue engineering. Part I. Traditional factors.", *Tissue Engineering*, 7(6):679-689 (2001).
Yang, et al., "The design of scaffolds for use in tissue engineering. Part II. Rapid prototyping techniques.", *Tissue Engineering*, 8(1):1-11 (2002).
Zeltinger, et al., "Effect of pore size and void fraction on cellular adhesion, proliferation, and matrix deposition.", *Tissue Engineering*, 7(5):557-572 (2001).
Zhang, et al., "Aligned porous structures by directional freezing", *Adv. Mater.*, 19:1529-1533 (2007).
Zhang, et al., "Poly($\alpha$-hydroxyl acids)/hydroxyapatite porous composites for bone-tissue engineering.", *J Biomed Mater Res*, 44:446-455 (1999).
Zhou, et al., "The thermal effects on electrospinning of polylactic acid melts", *Polymer*, 47(21):7497-7505 (2006).
Simonet, et al., "Ultra-porous 3D meshes by low-temperature electrospinning", poster presented by Technische Hochschule Zurich on a congress in Frankfurt am main, Germany, Oct. 23-25, 2006.

\* cited by examiner (a) (b)

(c)

(a) A-5

(b) B-5

(c) A-10

(d) B-10

(e) A-15

(f) B-15

Mandrel interface (23°C)

Air interface (23°C)

Mandrel interface (-15°C)

Air interface (-15°C)

Mandrel interface (-30°C)

Air interface (-30°C)

MANUFACTURING THREE-DIMENSIONAL SCAFFOLDS USING ELECTROSPINNING AT LOW TEMPERATURES

CROSS-REFERENCE TO RELATED APPLICATIONS

This application is a filing under 35 U.S.C. 371 of PCT/SG2007/000413 filed with the Patent Cooperation Treaty on Dec. 5, 2007, which claims the benefit of priority of U.S. provisional application No. 60/872,800, filed Dec. 5, 2006, the contents of each being hereby incorporated by reference in its entirety for all purposes.

FIELD OF THE INVENTION

The present invention refers to an apparatus and a method for the manufacture of a three-dimensional scaffold at low temperatures and the respective uses of the method and apparatus.

BACKGROUND OF THE INVENTION

Electrospinning had recently gained interest as a method of scaffold fabrication in tissue engineering (Pham, Q. P., Sharma, U. et al., 2006, Tissue Engineering, vol. 12, p. 1197-1211). In this process, long and fine threads are drawn from droplets of polymer by the application of a high voltage electric field (Li, D. & Xia, Y. N., 2004, Advanced Materials, vol. 16, p. 1151-1170). The result is a highly porous mesh of nanofibers that resemble the connective tissue in an extracellular matrix (Han, D. & Guoma, P. I.; 2006; Nanomedicine: Nanotechnology, Biology and Medicine; vol. 2, p. 37-41). This biomimicry has been shown to positively influence cell-scaffold interaction such as cell attachment, migration, proliferation and function (Lindberg, K. & Badylak, S. F., 2001, Burns, vo. 27, p. 254-266; Schindler, M. et al., 2005, Biomaterials, vol. 26, p. 5624-5631; Smith, L. A. & Ma, P. X., 2004, Colloids and Surfaces B-Biointerfaces, vol. 39, p. 125-131).

However, the major obstacle with the use of electrospun scaffolds is the lack of control of its pore size, which is inherently small (typically less than 5 µm). This is due to nature of the electrospinning process that randomly deposits layers of non-woven fibers on each other. Few researchers have addressed this issue, but it has several implications. Firstly, cell infiltration is poor as cells are unable to permeate through the small pores (Stankus, J. J., Guan, J. J., et al., 2006, Biomaterials, vol. 27, p. 735-744). Cell-scaffold interaction is thus limited to the surface whereas an ideal tissue engineered construct has to be three-dimensional. Secondly, the small pores prevent vascular ingrowth (Brauker, J. H. et al., 1995, Journal of Biomedical Materials Research, vol. 29, p. 1517-1524). This limits the thickness of the scaffold, as cells within the construct rely on diffusion from the vasculature for nutrient and waste transfer (Jain, R. K., Au, P., et al., 2005, Nature Biotechnology, vol. 23, p. 821-823; Levenberg, S. et al., 2005, Nature Biotechnology, vol. 23, p. 879-884). Thirdly, the lack of control of the pore size prevents one from optimizing the electrospun scaffold for its intended tissue application (Smith, L. A. & Ma, P. X., 2004, supra). This is because specific cell types interact optimally with the scaffold when it is of a certain pore size (Marshall, A. J. et al., 2004, Abstracts of Papers of the American Chemical Society, vol. 228, p. U386-U386). These factors limit the versatility of electrospun scaffolds in tissue engineering.

There have been two strategies used to improve cell infiltration into electrospun scaffolds. One is the use of filtration seeding bioreactors but these are complicated and result in an uneven cell distribution (Li, Y., Ma, T., Kniss, et al., 2001, Biotechnology Progress, vol. 17, p. 935-944). Stankus, J. J., Guan, J. J., et al. (2006, supra) adopted a different approach by simultaneously electro spraying cells in situ while electrospinning a polymeric mesh. With this microintegration technique, the group was able to obtain high cell densities within a thick construct, which could be maintained with a perfusion bioreactor. While these techniques improve cell density, they do not address the lack of vascularization when these constructs are implanted, as their pore size remains small.

Thus a need remains for the manufacture of electrospun scaffolds which meet the requirements for tissue engineering.

SUMMARY OF THE INVENTION

In a first aspect, the present invention refers to a method of manufacturing a three-dimensional scaffold using an apparatus for electrospinning comprising a high-voltage power supply; at least one spinneret connected to at least one container comprising a solution with at least one polymer dissolved therein; and a collector, wherein the method comprises:
  forming crystals from a molecule or group of molecules in vapor phase comprised in the surrounding atmosphere at the surface of the collector, wherein the collector has a temperature which allows formation of crystals at the surface of the collector;
  electrospinning the solution comprising at least one polymer dissolved therein around the crystals;
  continuing the formation of crystals and the electrospinning simultaneously; and
  removing the crystals by sublimation.

In another aspect, the present invention refers to a three-dimensional scaffold obtained by a method of the present invention, wherein the pore diameter of the scaffold is equal or greater than 5 µm.

In a further aspect, the present invention refers to the use of a three-dimensional scaffold of the present invention for tissue-engineering.

In yet another aspect, the present invention refers to an electrospinning apparatus for the manufacture of a three-dimensional scaffold of the present invention, comprising:
  a high-voltage power supply;
  at least one spinneret connected to a container comprising a solution with at least one polymer dissolved therein; and
  a collector;
wherein the collector has a temperature which allows formation of crystals at the surface of the collector, wherein the crystals are formed from a molecule or group of molecules in vapor phase comprised in the atmosphere surrounding the collector.

BRIEF DESCRIPTION OF THE DRAWINGS

The invention will be better understood with reference to the detailed description when considered in conjunction with the non-limiting examples and the accompanying drawings, in which:

As illustrated in FIG. 2, the pore size and porosity are controlled mainly by changing the rate of ice crystal formation at the collector and by changing the rate of fiber deposition during electro spinning.

FIG. 8 shows the in vivo cell infiltration and vascularization in scaffolds obtained from those rats. FIG. 8 shows hematoxylin and eosin staining of scaffolds implanted subcutaneously for 14 days. (a) Conventionally electrospun scaffold at 100× magnification, (b) conventionally electrospun scaffold at 400× magnification, (c) CES at 100× magnification and (d) CES at 400× magnification. (S: Scaffold, C: Capsule, M: Underlying muscle, B: Capillaries). represents 200 µm in (a) and (c) and 50 µm in (b) and (d). Panels e-h of FIG. 8 are grey scale versions of panels a-d of FIG. 8. Regions of the scaffolds infiltrated with cells are circled by the dotted lines.

FIG. 9 shows that the much thicker cryogenic electrospun scaffolds become much better diffusely infiltrated by 28 days than the thin conventional scaffold. represents 200 µm in (a) and (c) and 50 µm in (b) and (d). Panels e-h of FIG. 9 are grey scale versions of panels a-d of FIG. 9. Regions of the scaffolds infiltrated with cells are circled by the dotted lines.

FIG. 10 shows that the cells are limited to the periphery of the conventional electrospun scaffold even at 56 days (FIG. 10) whereas the cryogenic electrospun scaffold is completely penetrated by cells. represents 200 µm in (a) and (c) and 50 µm in (b) and (d). Panels e-h of FIG. 10 are grey scale versions of panels a-d of FIG. 10. Regions of the scaffolds infiltrated with cells are circled by the dotted lines.

As illustrated in FIG. 1, ice crystals formed on the mandrel at sub-zero temperatures are embedded within the electrospun mesh. The subsequent removal of the ice crystals through freeze-drying forms these pore structures within the electro spun mesh.

DETAILED DESCRIPTION OF THE INVENTION

Unlike other methods for generating nanostructures, the formation of a thin fiber via electrospinning is based on the uniaxial stretching (or elongation) of a viscoelastic jet derived from a polymer solution or melt. This technique is similar to the commercial processes for drawing microscale fibers except for the use of electrostatic repulsions between surface charges (rather than a mechanical or shear force) to continuously reduce the diameter of a viscoelastic jet or a glassy filament. Compared with mechanical drawing, electrostatic spinning is better suited for generating fibers with much thinner diameters, since the elongation can be accomplished via a contactless scheme through the application of an external electric field. Like mechanical drawing, electrospinning is also a continuous process and therefore should work well for high-volume production (Li, D. & Xia, Y. N., 2004, supra).

In electrospinning, a solid fiber is generated as the electrified jet (composed of a highly viscous polymer solution, see further below) is continuously stretched due to the electrostatic repulsions between the surface charges and the evaporation of solvent. As the fiber travels toward the surface of the collector, evaporation of the solvent in which the polymer is dissolved occurs and the fiber is typically dry when arriving at the surface of the collector (see FIG. 4).

Therefore, the terms "electrospinning" or "electrospun" as used herein refer to any method where materials are streamed, sprayed, sputtered or otherwise transported in the presence of an electric field. The electrospun solution comprising at least one polymer can be deposited form the direction of a charged container towards a grounded collector, or from a grounded container in the direction of a charged collector.

Figure 3:
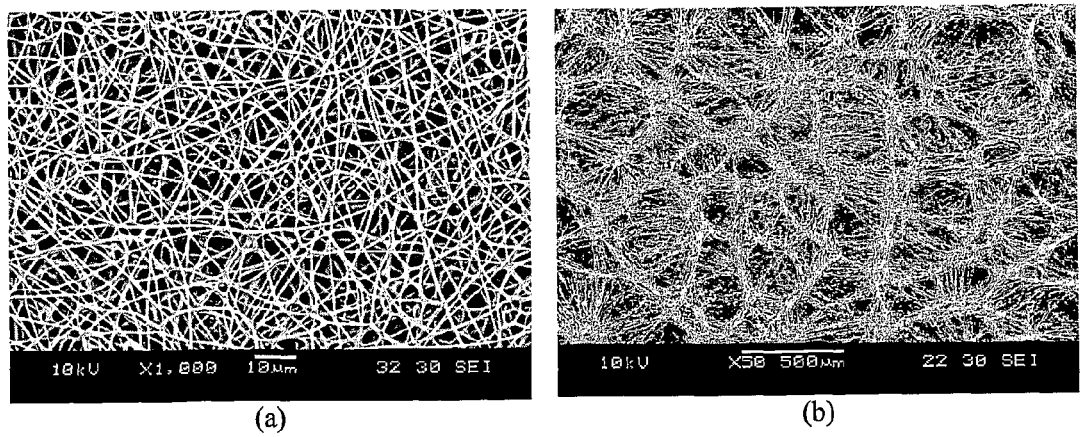
FIG. 3 shows SEM micrographs of (a) conventionally electrospun scaffold, (b) cryogenic electrospun scaffold (CES) and (c) oblique view showing three-dimensional structure of a pore in a cryogenic electrospun scaffold. Polymer scaffolds produced via conventional electrospinning (FIG. 3a) are characterized by a random polymer fiber mesh. However, the pore size between the fibers in such a polymer fiber mesh is only between several nanometer to a few micrometer. In contrast, the large pores obtained using the method of the present invention can measure between about 50 to 500 µm in size (FIG. 3b). However, pores obtained by the method of the present invention can exceed 500 µm. These pores are bounded by bundles of fibers that form a strut-like support. As can be seen from a SEM picture taken at an oblique view (FIG. 3c), the large pores have a three-dimensional spatial structure and are interconnected via their thin fibrous walls, which itself are porous like conventionally electrospun fibers.
Figure 12:
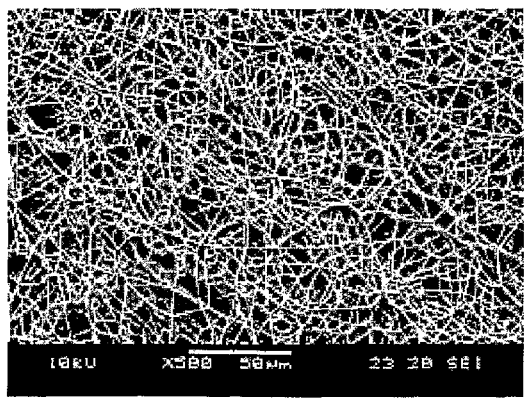
FIG. 12 shows the SEM micrographs of the cryogenic electrospun scaffolds collected at different mandrel temperatures. The two pictures in the top row show conventional electrospun scaffolds which were electrospun at 23° C. The left picture in the top row shows the mandrel interface whereas the right picture shows the air interface. For definition purposes it should be mentioned that the "mandrel interface" is the side of the scaffold facing the mandrel and the side of the scaffold facing the air is called the "air interface". In the middle row of pictures, the left picture shows the mandrel interface of a scaffold electrospun at −15° C. whereas the right picture shows the air interface of this scaffold. In the bottom row of pictures, the left picture shows the mandrel interface of a scaffold electrospun at −30° C. whereas the right picture shows the air interface of this scaffold. It can be observed that a conventional dense electrospun scaffold is obtained when the mandrel temperature is kept at 23° C. When the mandrel temperatures are −15° C. and −30° C., large pore structures (>5 µm) can be observed on both the mandrel and air interfaces of the scaffold.
Figure 12:
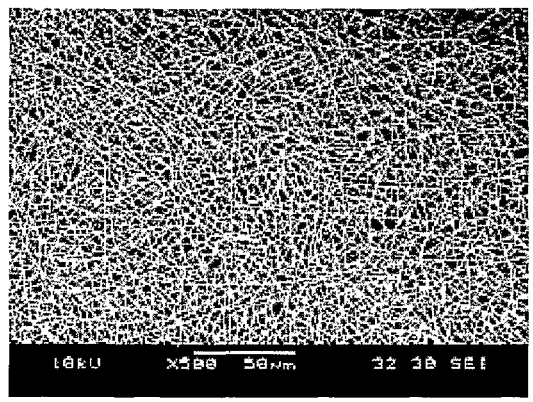
Figure 12:
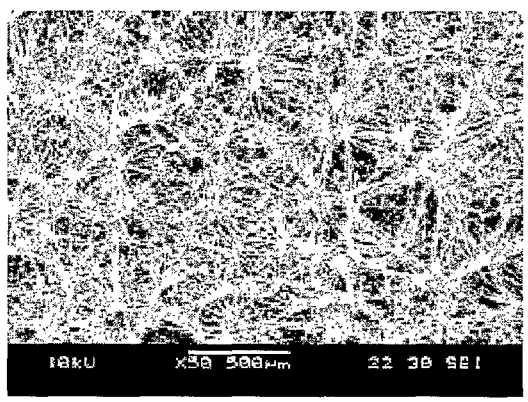
Figure 12:
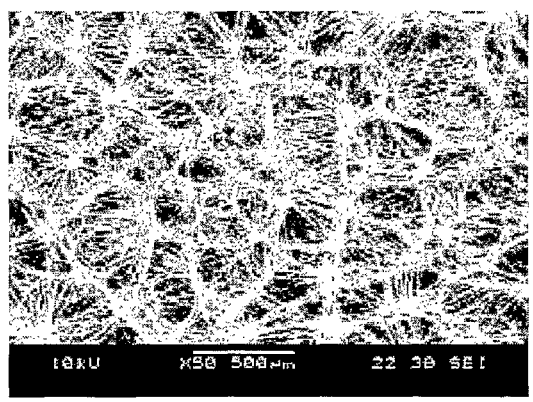
Figure 12:
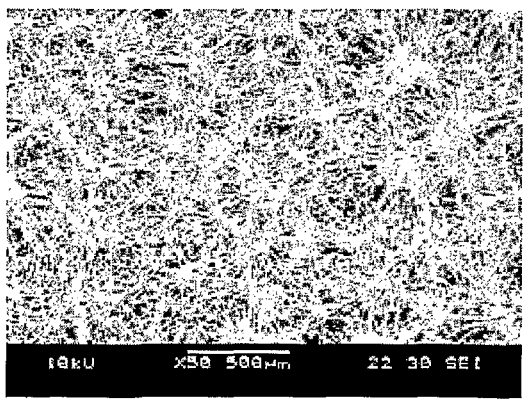
Figure 12:
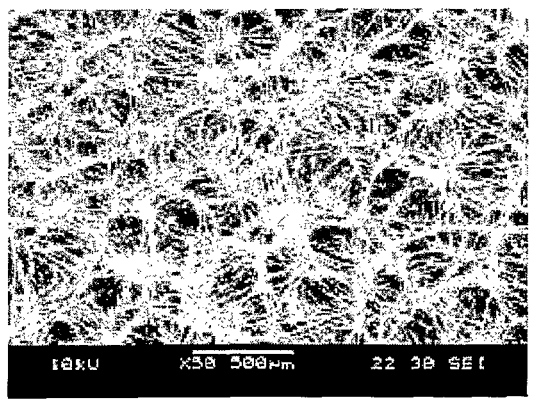

Polymer scaffolds produced via conventional electrospinning are characterized by a random polymer fiber mesh as illustrated by the SEM picture of such a mesh in FIG. 3a and the upper row in FIG. 12. However, the pore size between the fibers in such a polymer fiber mesh is only between several nanometer to a few micrometer.

As already mentioned in the introductory part, nano-scale to micro-scale pores sizes are needed in tissue engineering scaffolds. For example, Klawitter et al. reported (1976, J Biomed Mater Res, vol. 10(2), p. 311-323) that for adequate bone regeneration to occur in a scaffold, scaffold pore size needs to be at least 100 micrometer. It is generally known in the art that optimal bone regeneration occurs for pore sizes between 300 to 600 micrometer. Therefore new techniques have to be developed and incorporated into electrospinning to control or vary the pore sizes of the resulting mesh.

Obtaining such conditions using electrospinning is now possible due to the findings of the inventors of the present invention. According to the method of the present invention, a three-dimensional scaffold for tissue engineering is manufactured using an apparatus for electrospinning comprising a high-voltage power supply; at least one spinneret connected to at least one container comprising a solution with at least one polymer dissolved therein; and a collector, wherein the method comprises:

forming crystals from a molecule or group of molecules in vapor phase comprised in the surrounding atmosphere at the surface of the collector, wherein the collector has a temperature which allows formation of crystals at the surface of the collector;

electrospinning the solution comprising at least one polymer dissolved therein around the crystals;

continuing the formation of crystals and the electro spinning simultaneously; and removing the crystals by sublimation.

Formation of solid crystals at the surface of the collector can be achieved by either cooling the collector itself or by cooling the atmosphere surrounding the collector to an extent that solid crystals are formed at the surface of the collector.

This method provides for the design of electrospun scaffolds having different distributions of pore sizes in a single construct to cater for different requirements in basal membrane formation (nano-scale), tissue remodeling and regeneration (nano to micro scale), vascularization (micro scale) and cell in-growth (micro-scale).

When referring to "pores" in the context of the present invention, it is not referred to the pores which might be formed in the fibers which are spun but the size of the three-dimensional pores formed by the fibers as can bee seen in FIGS. 3b and 3c. A conventional electrospun scaffold as shown in FIG. 3a shows a highly porous network of non-woven submicron fibers in a planar orientation. The pores are bounded by individual fibers, and measure only between several nanometer to a few micrometer. In contrast, the large pores obtained using the method of the present invention measure in this illustrative example between about 50 to 500 µm in size (see FIG. 3b). However, it should be noted that pores obtained by the method of the present invention can exceed 500 µm. These pores are bounded by bundles of fibers that form a strut-like support. As can be seen from a SEM picture taken at an oblique view (FIG. 3c), the large pores have a three-dimensional spatial structure and are interconnected via their thin fibrous walls, which itself are porous like conventionally electrospun fibers.

The term "scaffold" as used herein, refers to an artificial structure capable of supporting a three-dimensional tissue formation. Scaffolds are supposed to resemble the connective tissue in an extracellular matrix. Thus, scaffolds allow for cell attachment, migration and growing of cells and synthesis of extracellular matrix components and biological molecules specific to the tissue targeted for replacement. To achieve those objects, a scaffold ideally provides a high porosity and proper pore size, a high surface area, biodegradability, proper degradation rate to match the rate of neotissue formation and it should provide a sufficient mechanical integrity to maintain the predesigned tissue structure. A scaffold should also not be toxic to the cells (i.e. biocompatible) and should positively interact with cells including enhanced cell adhesion, growth, migration, and differentiated function (Ma, P. X., May 2004, Materials Today, p. 30-40).

Figure 1:
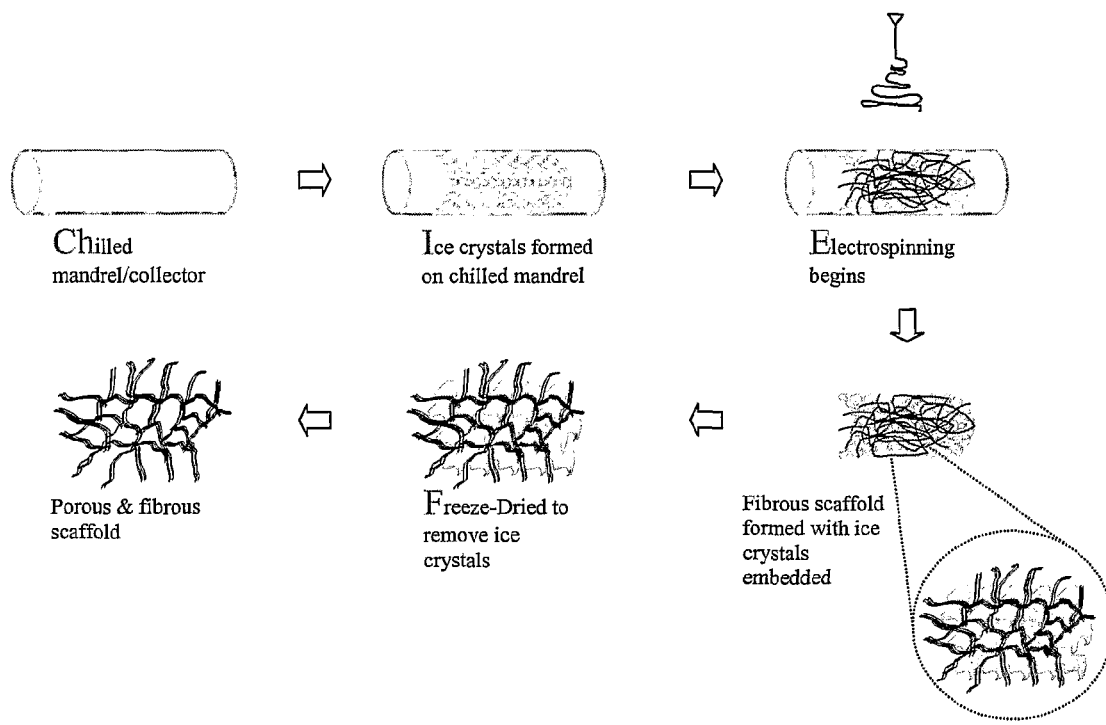
FIG. 1 shows a process flow of cryogenic electrospinning process (CHIEF). In the non-limiting example illustrated in FIG. 1, the method of the present invention involves the use of a collector that is chilled. Subsequently, ice crystals form on the surface of the chilled mandrel which serves as collector. After the first ice crystals have been formed electrospinning of the polymer solution starts. A fibrous scaffold forms with ice crystals embedded. After electrospinning is finished, the scaffold is freeze-dried to remove the ice crystals and obtain the three-dimensional scaffold.

Therefore, to further describe the method of the present invention and the characteristics of the scaffolds produced with it, it is referred to FIG. 1 showing an example which is given to illustrate the present invention. As can be seen from FIG. 1, the method of the present invention involves in this example the use of a collector that is cooled to subzero temperatures. In this particular example, a hollow rotating mandrel is used as collector. Solid crystals made of water ($H_2O$) from the surrounding atmosphere of the collector form on the collector and serve as a negative template around which electrospun fibers are deposited. After the scaffold reaches the desired form, the scaffold is subsequently dehydrated by freeze-drying to remove ice crystals, leaving behind a cryogenic electrospun scaffold (CES) with large pores (see FIGS. 3b and 3c). Further details for this illustrative example are given in the experimental section of this application.

Thus, this cryogenic electrospinning technique enables the fabrication of an electrospun scaffold with large pores, while retaining the nanofibrous structure that mimics the physical environment of the targeted tissue or organ to be replaced and which is required for cell growth, vascular ingrowth and tissue development.

The crystals which form at the surface of the collector can be made of any molecule or group of molecules in vapor phase which is/are comprised in the atmosphere surrounding the collector and which is/are deposited at the surface of the collector in form of solid crystals when the temperature at the surface of the collector is lowered to or below the freezing point of the molecule or group of molecules which is/are comprised in the atmosphere surrounding the collector. Since the question of forming crystals depends also on the pressure in the surrounding atmosphere, the pressure can be increased or decreased to support formation of crystals even at higher temperatures. Which pressure and temperature is most suitable to ease the freezing step of a certain group of molecules can be easily determined by a person skilled in the art when looking at the phase diagram of the molecule which shall form crystals at the surface of the collector.

In one example of the present invention, the crystals are ice crystals formed from water ($H_2O$) comprised in the surrounding atmosphere. After the scaffold reaches its final dimensions the crystals are removed by freeze-drying. Instead of water $D_2O$ can also be used. In another example, the crystals are formed from $CO_2$ comprised in the surrounding atmosphere. Other than the water ice crystals which are removed by freeze-drying, the $CO_2$ crystals are removed by sublimation. The sublimation temperature of carbon dioxide ($CO_2$) is $-78.5°$ C. at atmospheric pressure. If the electrospinning environment is filled with vapor $CO_2$, deposition of solid $CO_2$ crystals on the surface of the collector can be achieved if the collector is maintained at temperatures below $-78.5°$ C. After formation of the scaffold the crystals are removed from the scaffold through sublimation of $CO_2$ into vapor phase at room temperature.

The shape and thus the size of crystals depends also on the temperature at the surface of the collector or the surrounding of the collector. For example, water has a freezing point of $0°$ C. at atmospheric pressure. Just below freezing, at temperatures near $T=-2°$ C., the growth of ice crystals is plate-like, with thick plates at lower supersaturations, thinner plates at intermediate supresaturations, and plate-like dendritic structures at high supersaturations. For temperatures near $T=-5°$ C., the growth is columnar, with stout columns at the lower supersaturations, more slender, often hollow columns at intermediate supersaturations, and clusters of thin, needle-like crystals at higher supersaturations. Colder still, near $T=-15°$ C., the growth again becomes plate-like, and again one sees increasing structure with increasing supersaturation. Finally, at the lowest temperatures the growth becomes a mixture of thick plates at low supersaturations and columns at higher supersaturations. Growth of heavy water ($D_2O$) crystals from the vapour phase produces similar morphologies as a function of temperature, except shifted by approximately four degrees, in keeping with the isotopic shift in the freezing point between $D_2O$ and $H_2O$ (Libbrecht, K. G., 2005, Reports on Progress in Physics, vol. 68, p. 855-895).

Thus, the method of the present invention further comprises increasing or decreasing the temperature of the collector or the surrounding atmosphere of the collector as long as the temperature allows freezing of the molecules or group of molecules from the surrounding atmosphere at the surface of the collector.

In one example, illustrated further below, crystals have been formed by depositing water at the surface of the collector at a temperature of the collector of about $-15°$ C. or $-30°$ C. When the molecule to be deposited at the surface of the collector is water then the temperature should be below $0°$ C. at atmospheric pressure or between about $0°$ C. to about $-100°$ C. In another example, the temperature is between about $0°$ C. or $-1°$ C. to about $-30°$ C.

It is also important to note that the crystal growth in the method of the present invention can be enhanced when one let flow air over a growing surface of crystals, a phenomenon called the ventilation effect.

From the previous comments it also becomes obvious that not only the temperature can influence the crystal formation and thus the size and structure of the pores formed in the scaffold but also the saturation of the atmosphere with the elements or group of elements which are to be deposited on the surface of the collector.

Thus, in a further aspect of the present invention the method further comprises increasing or decreasing the saturation of the atmosphere with the molecules or group of molecules which are to be deposited on the surface of the collector.

As demonstrated in the examples (see also FIGS. 4a to 4c), when increasing the saturation of the atmosphere surrounding the collector with water (i.e. humidity), the size of the three-dimensional pores is larger and more defined.

The "atmosphere" surrounding the collector can be varied to contain, for example, the specific molecules or group of molecules which are to be deposited on the surface of the collector or to vary the saturation of the atmosphere with the specific molecules or group of molecules to be deposited at the surface of the collector. In one example, referred to further below, normal air forms the atmosphere surrounding the collector. In another example, mentioned herein, nitrogen ($N_2$) is added to the atmosphere to control the water content in the air. A pure $CO_2$ atmosphere would for example also be possible.

In one aspect the present invention is directed at a method in which the crystals which are to be formed on the collector are formed by directing a jet of vapor dispensed by at least one spinneret at the collector.

A jet of vapor which can be made of a molecule or group of molecules of inorganic or organic material can be directed at the chilled collector. The chilled collector is maintained at a temperature and pressure such that the vapor can be deposited as solid crystals, without passing through the liquid phase. The vapor can be deposited by spraying a jet of vaporized solvent through an orifice (maintained above the boiling point of the solvent) towards the collector. The method of organic vapor deposition has been previously described for example by Sun, Y. R., Shtein, M., et. al. (2005, Applied Physics Letters, vol. 86(11), p. 13504). An inert carrier gas, such as nitrogen, can be used to deliver the vapor through the orifice. The ratio of the vapor to the carrier gas will determine the amount of crystals that are deposited at the chilled collector. The organic crystals are subsequently removed by sublimation at the sublimation temperature and pressure of, for example, the organic substance, thus preserving the three-dimensional pore structure of the electrospun scaffold. This method allows localized deposition of organic crystals with a directed jet of the organic vapor. This enables the customization of the pore structures within the scaffold, with regions of high porosity and larger pore sizes created by depositing more crystals in those regions. In general, non-flammable organic substances can be used for this method.

Figure 2:
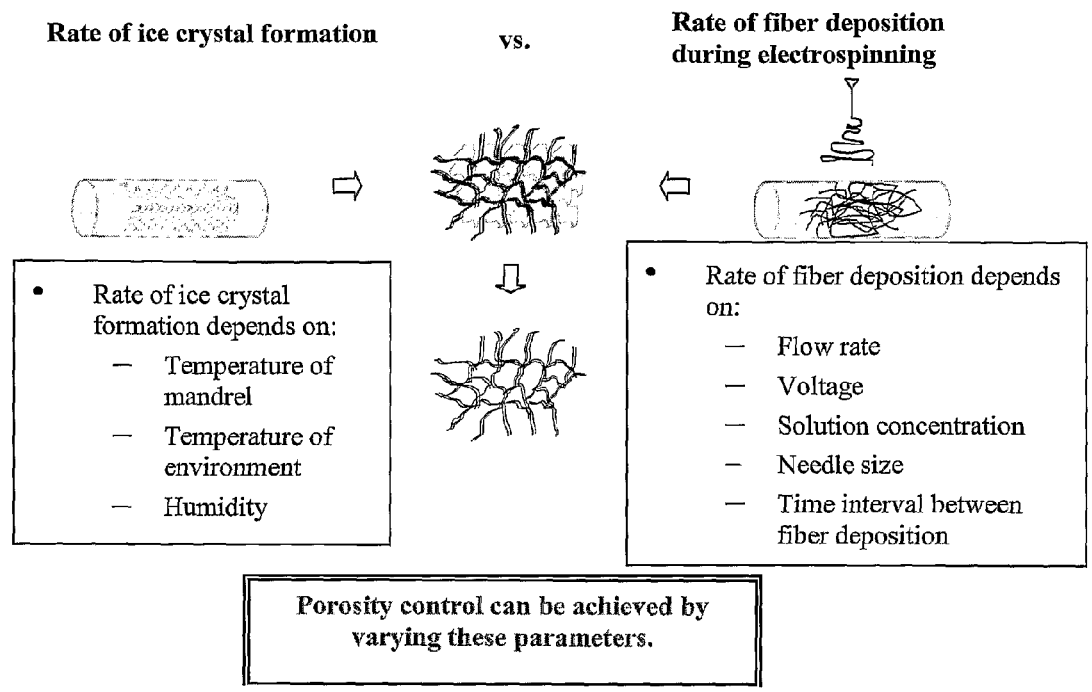
FIG. 2 shows the factors affecting pore size and porosity of cryogenic electrospun scaffolds.

Some other factors which can influence the structure and size of the pores formed by the electrospun fibers are summarized in FIG. 2.

Thus, in another aspect the method of the present invention further comprises increasing or decreasing the flow rate of the solution comprising the at least one polymer dissolved therein. The flow rate of the solution or in other words the solution feeding rate can be changed by increasing or decreasing the pressure in the at least one container comprising the at least one polymer dissolved therein. In general, a higher feeding rate for the solution leads to the formation of thicker fibers.

In general, the diameter of fibers affects the surface area of the fibers, which in turn affects the rate of degradation of the scaffold material. The mechanical properties of the electrospun mesh can also be affected by the diameter of the fibers. In the present invention, varying solution flow rate also changes the pore size and porosity of the eventual scaffold. To elaborate, if one increases solution flow rate while keeping all other parameters constant, there is more throughput of polymer through the spinneret which will occupy more space with respect to the deposited crystals. In this way, the pore size and the porosity of the scaffold will decrease with increasing flow rate of the solution.

In still another aspect the method of the present invention further comprises varying the time interval between electrospinning and the formation of crystals. It can be easily imagined that the rates of crystal formation and fiber deposition are two competing factors that can have an effect on the pore structure of the cryogenic electrospun scaffolds. As more time passes between different electrospinning steps larger crystals can grow on the collector which means that the resulting pores of the scaffold are growing larger. To demonstrate the effect of the relative rates of crystal formation and fiber deposition on the pore structure of the cryogenic electrospun scaffold, the time interval between fiber deposition has been varied in an example conducted by the inventors (see further below). A greater time interval between spinning steps allows ice crystals to grow in size, hence resulting in larger pores in the cryogenic electrospun scaffold.

Figure 8:
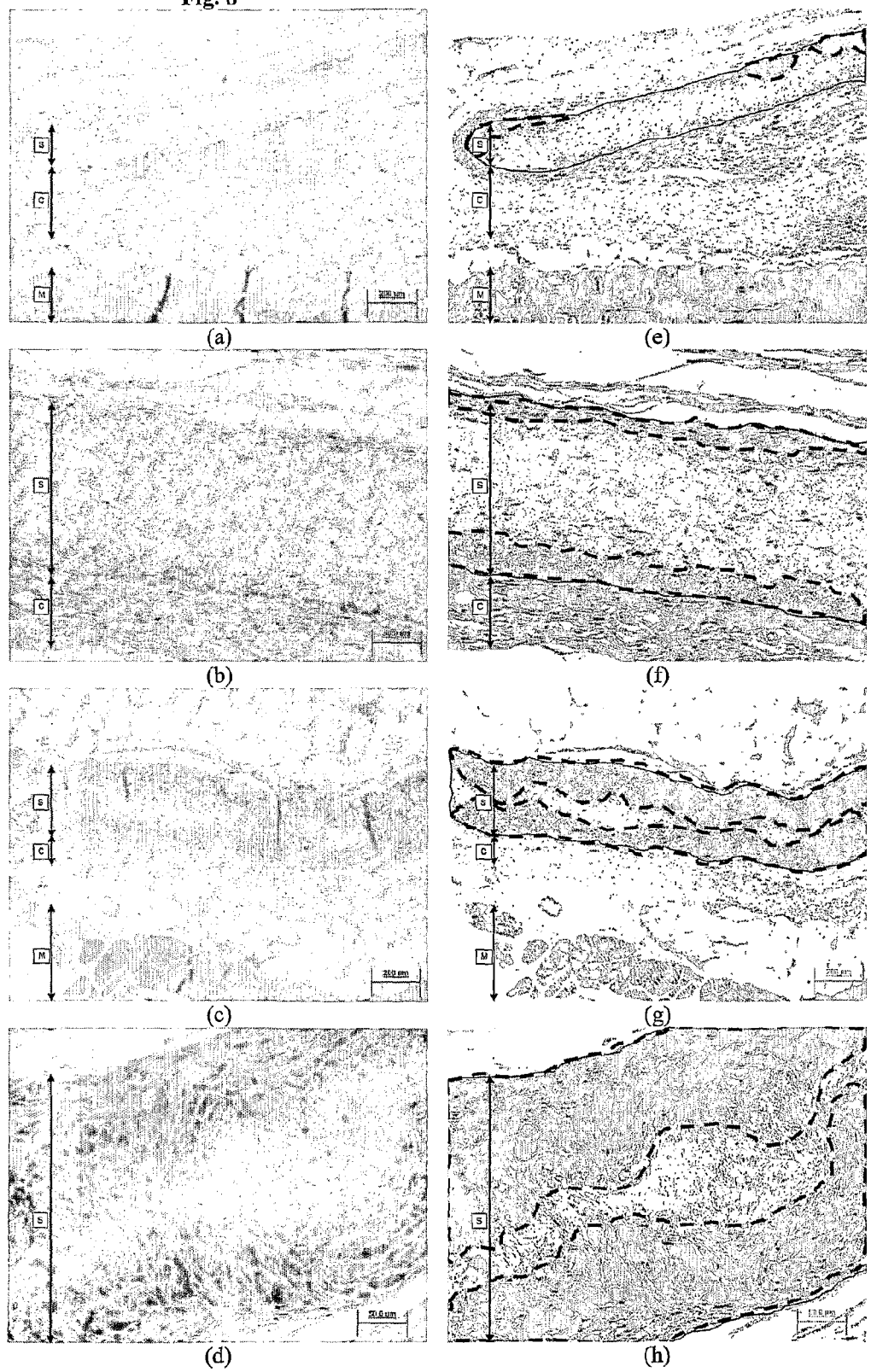
FIG. 8 shows the results of in vivo experiments in which conventional electrospun scaffold and CES were implanted in rats.

Thus, by varying the time intervals between different spinning steps, a scaffold with different layers having different pore sizes formed by the fibers can be manufactured. This is a great advantage for the manufacture of scaffolds because other methods for the manufacture of scaffolds result, in general, in very uniform structures with one defined pore size or range of pore sizes. Those conventional scaffolds are normally not so thick because cells grow only in the outer layers of the scaffold. Therefore, it is possible with the method of the present invention to design a thicker scaffold which mimics the in vivo structure of an extracellular matrix in more detail. As demonstrated by the following examples, the scaffolds of the present invention allow cells to grow all over the scaffold and also allow sufficient vascularization within the scaffold (see for example FIGS. 8 and 9).

In addition, it is possible to design a scaffold wherein the different layers are made of different polymers. For example, it is possible to create a three-layered design that consists of two electrospun dense scaffolds which need a shorter time for degradation compared to an electrospun scaffold which is sandwiched in between these two other scaffolds. For example, the dense scaffolds can be made of biomaterials that degrade in two weeks while the scaffold sandwiched in between can be made of another biomaterial that has a slower degradation rate. The dense scaffolds keep the inflammatory cells at the periphery of the construct and prevent them from infiltrating the implanted construct. After the inflammatory stage (approximately 2 weeks), the dense scaffolds will degrade and fibrosis takes place. Fibroblasts infiltrate the sandwiched scaffold and deposit collagen within the sandwiched scaffold. In this way, there will be fewer inflammatory cells that infiltrate the sandwiched scaffold and the construct will only consists of fibroblasts and collagen.

In another example, it is also possible that an electrospun scaffold designed according to the method of the present invention is sandwiched between two other scaffolds as described above but wherein those two other scaffolds are not electrospun scaffolds but are scaffolds that are commercially available. It is also possible to form a thin polymer formed by coacervation of a polymer at the surface of the electrospun scaffold. Polymer coacervation and polymers used for it are described for example in US 2006/0019362 A1.

Furthermore, different tissues require scaffolds with different pore sizes. As described previously, it is generally known in the art that optimal bone regeneration occurs for pore sizes between 300 to 600 micrometer. On the other hand for an optimal ingrowth of blood vessels pore sizes of about 35 to 50 µm are required (Marshall, A. J., et al., 2004, supra). Using the method of the present invention, scaffolds obtained by electrospinning having such pore sizes can be easily manufactured.

However, further parameters are disclosed in FIG. 2 which, when changed, can influence the structure of an electrospun scaffold obtained by the method of the present invention. Thus, the method of the present invention further comprises varying at least one of the parameters selected from the group consisting of needle size and design, voltage and the concentration of the at least one polymer in the solution.

Changing the voltage applied during electrospinning can influence the diameter of the fibers produced. As described by Megelski S. et al. (2002, Macromolecules, vol. 35, no. 22, p. 84.56-8466) and Pham, Q. P. et al. (2006, Tissue Engineering, vol. 12, no. 5, p. 1197-1211) the diameter of a fiber can be decreased with increasing the spinning voltage, whereas decreasing the spinning voltage increases the diameter of a fiber. At low voltage of field strengths, a drop of the solution comprising the at least one polymer dissolved therein is typically suspended at the tip of the spinneret, i.e. needle tip. A jet will originate from the Taylor cone ("Taylor cone" refers to the droplet produced at the tip of the needle (see FIG. 4) when an electric field is applied. G. I. Taylor showed 1969 that this droplet is a cone-shaped and the jets are ejected from the vertices of the cone) producing spinning (assuming that the force of the electric field is sufficient to overcome the surface tension of the solution). Using laser diffraction, it has also been shown that increased voltages can produce jets with larger diameters and ultimately lead to the formation of several jets (Demir, M. M., Yilgor, I. et al., 2002, Polymer, vol. 43, p. 3303 et seqq.)

In the method of the present invention, the voltage applied can be in a range of 0 kV to 50 kV or 7 kV up to 35 kV. In one example, a voltage between 10 and 35 kV has been applied. The voltage across the electrodes is usually varied together with other parameters of the electrospinning process. For example, when the distance between the spinneret and collector is increased, the voltage has to be increased to sustain the Taylor cone at the spinneret.

Several designs and configurations of needle tips have been investigated for the electrospinning process (Pham, Q. P., Sharma, U. et al., 2006, supra). For example, a coaxial, two-capillary spinneret was designed. Using polymer feeds consisting of two immiscible liquids, it was possible to produce hollow nanofibers. With this two-capillary spinneret it was also possible to prepare blends of polymers. The use of multiple tips has also been investigated as a way to increase the throughput and production rate of electrospinning of poly (ethylene oxide) (PEO). Multiple needle tips have also been used to prepare blends of poly(vinyl alcohol) (PVA) and cellulose acetate. Using four tips and varying the number containing PVA and cellulose acetate allowed for fibers with various weight ratios of PVA and cellulose acetate to be produced. Using two tips and a collector that could move transversely, mixes of PEO and polyurethane fibers have been spun. The transverse motion of the collector allowed for more uniform distribution of each polymer.

The concentration and thus the viscosity of the solution comprising the at least one polymer has also been examined. Megelski S. et al. (2002, supra) reported that the fiber diameter increases with increasing solution concentration. Both concentration and viscosity of the polymer solution are parameters that can be changed to provide for a steady Taylor cone and consequently, a stable electrospinning process. Changing the concentration of the solution can also affect the morphology of the electrospun fibers. In general, increasing the solution concentration while keeping all other parameters for electrospinning constant result in a slower flow rate of the solution.

The method of the present invention is not limited to a specific kind of polymer for electrospinning. Every known polymer which is suitable for electrospinning or can be made suitable for electrospinning can be used in the method of the present invention. A list of electrospun polymers suitable for the method of the present invention is listed for example in Table I of the article of Subbiah, T. and Bhat, G. S. et al. (2005, Journal of Applied Polymer Science, vol. 96, p. 557-569).

Due to the use of the scaffolds in cell biology and tissue engineering, the polymers used in the method of the present invention can also be biocompatible and/or biodegradable. "Biodegradable" refers to material that can be absorbed or degraded in a patient's body. "Biocompatible" refers to materials that do not have toxic or injurious effects on biological functions.

A large number of suitable biocompatible polymers is known and can be selected from the group consisting of poly(urethanes), poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly (vinyl acetate), polyacrylamide, poly(ethylene-co-vinyl acetate), poly(ethylene glycol), poly(methacrylic acid), poly-lactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO) and polyorthoesters. It is also possible to use blends of different polymers listed above. In one, non limiting example of the present invention, PLA is used which has been dissolved in 1,1,1,3,3,3-hexafluoroisopropanol (HFIP).

In matrices composed of electrospun elastin (for elasticity), electrospun collagen (to promote cell infiltration and lend mechanical integrity), and other components, such as PLGA, PEO, PVA, or other blends, the relative ratio of the different components in the matrix can be tailored to specific applications (e.g. more elastin, less collagen depending on the tissue to be engineered).

Representative materials for forming the biodegradable material include natural or synthetic polymers, such as, collagen, poly(alpha esters) such as poly(lactate acid), poly(g-lycolic acid), polyorthoesters, polyanhydrides and their copolymers, which degrade by hydrolysis at a controlled rate and are reabsorbed. These materials provide the maximum control of degradability, manageability, size and configuration.

Other biodegradable materials can be selected from the group consisting of cellulose ether, cellulose, cellulose ester, chitosan, gelatin, fluorinated polyethylene, poly-4-methyl-pentene, polyacrylonitrile, polyamide, polyamideimide, polyacrylate, polybenzoxazole, polycarbonate, polycyanoarylether, polyester, polyestercarbonate, polyether, poly-etheretherketone, polyetherimide, polyetherketone, poly-ethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

Another group of polymers that can be used in the method of the present invention are polymers having amino acids (e.g. lysine or RGD sequence) or peptides (polypeptides or polypeptides co-polymer) added to the polymer backbone or grafted onto the surface of the polymers to promote cell material interactions. Such materials are described for example in the article of Deng, X. M., Liu, Y., et al. (2002, European Polymer Journal, vol. 38(7), p. 14.35-1441). One example of such a polymer would be poly/DL-lactic acid)-co-polyethylene glycol)-co-poly(L-lysine)copolymer.

As limited by their molecular weights and/or solubilities, some functional polymers are not suitable for use with electrospinning. One strategy for solving this problem is to blend them with polymers that are well-suited for electrospinning. Based on this approach, Kaplan and coworkers (2002, Biomacromolecules, vol. 3, p. 1233 et seqq.) have successfully fabricated protein-carrying fibers by adding the proteins to the solution of a conventional polymer. Fibers consisting of blends between polyaniline (or polythiophene) with conventional organic polymers have also been investigated. Blending was found to be fruitful in improving some properties or applications associated with fibers. For instance, it has been demonstrated that the physical and biological properties (e.g., biodegradation rate and hydrophilicity) of PLA fibers could be finely tuned by simply controlling the compositions of polymer blend solutions used for electrospinning (Kim, K. Yu, M. et al., 2003, Biomaterials, vol. 24, p. 4977 et seqq.)

The use of biocompatible and/or biodegradable polymers will depend on given applications and specifications required. A more detailed discussion of such polymers and types of polymers can also be found in Brannon-Peppas, Lisa, "Polymers in Controlled Drug Delivery," Medical Plastics and Biomaterials, November 1997, which is incorporated herein by reference.

Sometimes it is necessary to dissolve a polymer before it can be used for electrospinning. Therefore, the at least one polymer used in the method of the present invention can be dissolved in an inorganic solvent or an organic solvent. Exemplary solvents which are known in the prior art can be selected from the group consisting of acetone, N,N-dimethylformamide (DMF), water/chloroform, water, methylethylketone, silk aqueous solution, acetic acid, formic acid, ethanol, diethylformamide, methylene chloride together with dimethyl formamide, dimethyl formamide:toluene (1:9), water/ethanol or NaCl, hydrochloric acid, camphorsulfonic acid, dichloromethane mixed with trifluoroacetic acid, chloroform, dimethylacetamide, dimethyl formamide:tetrahydrofuran (1:1), dichloromethane, tetrahydrofuran (THF), N,N-dimethyl acetamide (DMAc), 1,1,1,3,3,3-hexa fluoro-2-propanol (HFIP), HFIP mixed with DMF, isopropyl alcohol (IPA), sulphuric acid, and mixtures thereof. As previously mentioned, those solvents evaporate during electrospinning. In a non limiting example of the present invention HFIP is used to dissolve PLA. In Table 1 of a review article of Huang, Z.-M., Kotaki, M. and Ramakrishna, S. (2003, Composites Science and Technology, vol. 63, p. 2223-2253) at page 2226-2230, a list of polymers together with a possible solvent is given. Another example is the list referred to in the article of Subbiah, T., et al. (2005, Table I, supra). These articles and in particular the content of Table I is incorporated by reference into the present application. It should be noted that these lists illustrate only exemplary combinations of polymers and solvents and that a person skilled in the art would know how to create further or different combinations than the one mentioned in these articles.

Organic solvents could be, for example, acetone, N,N-dimethylformamide (DMF), diethylformamide, chloroform, methylethylketone, acetic acid, formic acid, ethanol, 1,1,1,3, 3,3-hexa fluoro-2-propanol (HFIP), tetrafluoroethanol, dichloromethane (DCM), tetrahydrofuran (THF), trifluoroacetic acid (TFA), camphorsulfonic acid, dimethylacetamide, isopropyl alcohol (IPA) and mixtures thereof. Examples of mixtures would be DCM with DMF, DMF:Toluene (1:9), ethanolNaCl, DCM mixed with TFA, DMF:THF (1:1) and HFIP mixed with DMF.

Inorganic solvents could be, for example, water, hydrochloric acid, sulphuric acid and mixtures thereof. Examples of mixtures of inorganic solvents would be water/NaCl and water/chloroform.

Since the collector used herein is chilled or the surrounding atmosphere is cooled to subzero temperatures, rapid evaporation of the solvent for the polymer is not necessary as the polymer fibers will solidify and phase separate from the solution. Hence, non-volatile solvents can be used in the solution. A non-limiting example would be polyurethane (PU) dissolved in dimethyl formamide (DMF) (boiling point=153° C., freezing point=−61° C.). Electrospinning is carried out at ambient temperature (approximately 23° C.) while the collector is maintained at temperatures below −61° C. The fiber (consisting of PU/DMF) solidifies on the collector and the PU will phase separate from the DMF.

For some applications it might be of some advantage not to use solvents. In these cases polymer melts can be used alternatively. Thus, the present invention is also directed to a method wherein a polymer melt is electrospun. For the method of the present invention the use of polymer melts is not limited to a specific polymer melt. For example, polymers, such as polylactic acid) (PLA), polyethylene (PE), polypropylene (PP), nylon 12 together with PA-12, polyethylene terephthalate (PET), polyethylene naphthalate (PEN), polyethylene terephthalate together with polyethylene naphthalate, and polycaprolactone together with poly(ethylene oxide-block-ε-caprolactone) (PEO-b-PCL) can be used in melted forms.

Polymer melts are known to a person skilled in the art and are described, for example, in the article of Huang, Z.-M., Kotaki, M. and Ramakrishna, S. (2003, supra), Table II and Dalton, P. D., Klinkhammer, K. et al. (2006, Biomacromolecules, vol. 7, no. 3, p. 686-690).

The processing temperature for polyethylene (PE) is about 200 to 220° C., about 200 to 240° C. for polypropylene (PP), about 220° C. for nylon 12 together with PA-12, about 270° C. for polyethylene terephthalate (PET), about 290° C. for polyethylene naphthalate (PEN), about 290° C. for polyethylene terephthalate together with polyethylene naphthalate (75/25 or 25/75 (wt. %)), and about 85° C. for polycaprolactone together with poly(ethylene oxide-block-ε-caprolactone) (PEO-b-PCL) (20:80). The melting temperature of PLA melt is about 200° C. For example, PLA is commonly used in biomedical applications and is described for example by Zhou, H. J., Green, T. B., et al. (2006, Polymers, vol. 47(21), p. 7497-7505).

It is further possible to enhance attachment of cells to the biocompatible or biodegradable substrate by coating the scaffold matrix with compounds such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. Mechanical and biochemical parameters ensure the matrix provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow vascular ingrowth or ingrowth of the lymphatic network or nerve fibers, and drugs, can be incorporated into the matrix of the scaffold or provided in conjunction with the matrix. Similarly, polymers containing peptides such as the attachment peptide RGD (Arg-Gly-Asp) can be synthesized for use in forming matrices.

In general it is also possible to add a variety of functional components directly to the solution for electrospinning to obtain fibers with a diversified range of compositions and well-defined functionalities. In particular components which can support the ingrowth of cells into the scaffold can be incorporated. Those components can be applied either by mixing them directly with the solution or by applying the additional components simultaneously or subsequently through another container onto the collector. For example, biological molecules such as fibronectin and laminin can be incorporated within the electrospun mesh to promote cellular activities such as attachment and migration. The final freeze-drying step serves to lyophilize the molecules, which might help to preserve the proteins in the fibrous mesh. In order to integrate cells into the electrospun mesh, the freeze drying step is preferably excluded. This means that the process has to use other vapor molecules as the templating crystals. For example, a technique that uses $CO_2$ could be used as the crystals are removed by sublimation at room temperature without freeze drying. In this way, the viability of the cells can be easily maintained.

In case it is necessary, it is possible to use a cryoprotectant which can be used to prevent cells from freezing damage at low temperatures. Typically, the cryoprotectant used is dimethylsulfoxide (DMSO) in culture medium (e.g. 10% DMSO in 90% culture medium by volume). Gelatin is another example of cryoprotectant that can be used. The cells suspension can be electrosprayed from a spinneret towards the collector, with the electrospun fibers coming from another spinneret simultaneously. This method of integrating cells into electrospun scaffold is known in the prior art as microintegration (Stankus, J. J., Guan, J. J., et al., 2006, Biomaterials, vol. 27(5), p. 735-744). However, the method of the present invention is unique as the collector is chilled and the cells are collected at low temperatures. Since cells are generally stored in liquid nitrogen, the cryogenic step will improve cell viability within the electrospun mesh.

The sublimation step in the method of the present invention is carried out to remove the solid crystals formed on the collector and which are responsible for forming the pores within the scaffold. Sublimation can be carried out, for example by freeze-drying (also known as lyophilization). Freeze drying works by freezing the material and then reducing the surrounding pressure and adding enough heat to allow the frozen compound in the material to sublime directly from the solid phase to gas.

Different kinds of freeze dryers can be used for the purposes of the present invention, such as rotary evaporators, manifold freeze dryers, or tray freeze dryers.

Optionally it is possible in the method of the present invention to include a further step of drying after the freeze-drying step to remove residual solvent which still remained in the scaffold.

In another aspect, the present invention is also directed to a three-dimensional scaffold obtained by a method of the present invention, wherein the pore diameter of the scaffold is equal or greater than 5 µm. As previously mentioned, different applications require different pore sizes. For example, the following pore sizes have been reported to be optimal for the specific applications: about 5 µm for neovascularization, between about 5 to about 15 µm for fibroblast ingrowth, about 20 µm for hepatocyte ingrowth, between about 20 to 125 µm for skin regeneration, between about 70 to 120 µm for chondrocyte ingrowth, between about 40 to 150 µm for fibroblast binding, between about 45 to 150 µm for liver tissue regeneration, between about 60 to 150 µm for vascular smooth muscle cell binding, between about 100 to 300 µm for bladder smooth muscle cell adhesion and ingrowth, between about 100 to 400 µm for bone regeneration and between about 200 to 350 µm for osteoconduction. With the method of the present invention pore sizes of this size or within this range can be obtained. It should be understood that depending on the application, pore sizes other than the pore sizes or range of pore sizes mentioned above are possible.

Those scaffolds can be made of a biocompatible and/or biodegradable material which is mentioned above. As also previously mentioned, due to the multiple possibilities of adapting the structure of the scaffold by varying the parameters for its manufacturing mentioned above, the scaffold of the present invention can consist of different layers with different pore sizes.

Even though those scaffolds might also be used outside the field of tissue engineering, they are preferably used for tissue engineering purposes. Therefore, the scaffold of the present invention might be seeded with one or more eukaryotic cell lines. Depending on the tissue which the applicant wishes to develop in and on the scaffold a person skilled in the art will know which cell line or cell lines can be seeded onto the scaffold. As previously mentioned it is also possible to add further components and bioactive factors to the scaffold to enhance development and growing of cells seeded on the scaffold.

For example, the scaffolds of the present invention can be seeded with fibroblasts for skin regeneration or bone marrow stem cells for bone development.

In another aspect, the present invention also refers to the use of the scaffolds of the present invention for tissue-engineering purposes. Those, scaffolds can be used in different applications, for example as skin replacement or bone replacement. Those scaffolds can be used to provide an ECM like structure which supports cell growth and thus regeneration of the damaged tissue. It can also be used in applications which require high cell density and the presence of vasculatures such as engineered muscle tissues (Levenberg, S. et al., 2005, supra).

The flexibility in the method of the present invention also allows the fabrication of functionally graded (in terms of pore size) electrospun scaffolds. For example, a bilayered electrospun construct consists of a dense section (pore size<5 µm) made by conventional electrospinning and an open cryogenic electrospun scaffolds section (pore size>5 µm). The dense section acts as a basal membrane which supports attachment, proliferation and differentiation of epithelial and endothelial cell types while the open section provides a three-dimensional structure for fibroblasts and muscle cells infiltration. This bilayered concept finds its application in several tissue engineering applications such as skin, (epidermal keratinocytes/dermal fibroblast), esophagus (Jansen, P. L. et al., 2004, European Surgical Research, vol. 36, p. 104-111) (epithelial cells/muscularis mucosa and externa muscle cells) and blood vessels (Lheureux, N., Germain, L. et al., 1993, Journal of Vascular Surgery, vol. 17, p. 499-509) (endothelium/smooth muscle cells).

The scaffolds can also be used for localized delivery of therapeutic agents as well as controlled release of such agents at the target site in a subject.

The present invention also refers to an electrospinning apparatus for the manufacture of a three-dimensional scaffold of the present invention, comprising
  at least one high-voltage power supply;
  at least one spinneret connected to a container comprising a solution with at least one polymer dissolved therein; and
  a collector;
wherein the collector has a temperature which allows formation of crystals at the surface of the collector, wherein the crystals are formed from a molecule or group of molecules comprised in the atmosphere surrounding the collector.

Figure 4:
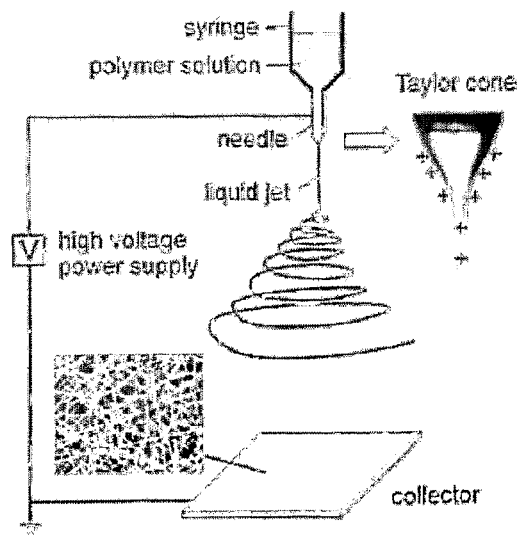
FIG. 4 shows a schematic illustration of the basic setup for conventional electrospinning. The insets show a drawing of the electrified Taylor cone and a typical SEM image of a non-woven mat of nanofibers deposited on the collector.

FIG. 4 shows a schematic illustration of the basic setup of an apparatus for electrospinning. FIG. 4 shows the four major components: a high-voltage power supply, a spinneret (i.e. a metallic needle), and a collector (a grounded conductor). Direct current (DC) power supplies are usually for electrospinning although the use of alternating current (AC) potentials is also feasible.

The spinneret is connected to a syringe in which the polymer solution (or melt is hosted). It is possible to use more than one spinneret, for example, 1, 2, 3 or 4 spinnerets, which are connected to a syringe or container comprising the polymer solution or melt. More than one spinneret is specifically advantageous if several kinds of polymers are ought to be applied together and those polymers are not dissolvable in the same solvent.

With the use of a syringe pump, the solution can be fed through the spinneret at a constant and controllable rate. When a high voltage (usually in the range of 1 to 35 kV) is applied, the pendent drop of polymer solution at the nozzle of the spinneret will become highly electrified and the induced charges are evenly distributed over the surface. As a result, the drop will experience two major types of electrostatic forces: the electrostatic repulsion between the surfaces charges; and the Coulomb force exerted by the external electric field. Under the action of these electrostatic interactions, the liquid drop will be distorted into a conical object commonly known as the Taylor cone. Once the strength of the electric field has surpassed a threshold value, the electrostatic forces can overcome the surface tension of the polymer solution and thus force the ejection of a liquid jet from the nozzle. This electrified jet then undergoes a stretching and whipping process, leading to the formation of a long and thin thread. As the liquid jet is continuously elongated and the solvent is evaporated, its diameter can be greatly reduced from hundreds of micrometers to as small as tens of nonometers. Attracted by the grounded collector placed under the spinneret, the charged fiber is deposited on the collector.

The orifice of the metallic needle (spinneret) can be of different size depending on the final diameter of the fiber which is desired to deposit on the collector. In general, the size of the needle used for electrospinning depends on the concentration and viscosity of the solution. A person skilled in the art is able to select the correct needle size to obtain the optimal conditions for electrospinning. In the examples of the present invention, the needle sizes range from 21 to 26 gauges. In one example a needle size of 26 G is used.

This needle(s) can be connected to one or more container depending on how many polymer streams are supposed to be fed through one needle. Preferably, each needle is connected to one container comprising a polymer solution.

The material the collector is made of is not limited to any specific material. The collector can be made of any material which is suitable for electrospinning. In general collectors are made of metal; however, they can also be made of other materials, such as paper or even a human hand (Pham, Q. P., Sharma, U. et al., 2006, supra). It was found that smooth fibers were obtained when metal collectors were used. A copper mesh and aluminum foil are further examples for materials which can be used for a collector.

The design of the collector can also be varied depending on the purpose of its use. It was previously described (Pham, Q. P., Sharma, U. et al., 2006, supra) that two parallel plates can be used when spinning fibers in order to generate uniform electric fields. Frame collectors have been shown to yield aligned fibers with a conductive frame producing better alignment than a non-conductive one. Also, an array of electrospun fibers has been produced using two conductive, collection rings. The fibers have been suspended between the rings, and fibers up to 10 cm long have been obtained. In one example it was also demonstrated that PEO can be spun using a multiple field method in which the polymer jet passed through three parallel rings, each connected to an independent power supply. This method produced smaller fibers that collected in a more focused area. Thus, the apparatus of the present invention can use more than one power supply. Furthermore, this would be important when different solutions are used which require different field strength in order to be electrospun.

Fibers have also been collected using a rotating cylindrical drum collector rather than a stationary target. Thus, the collector used in the apparatus of the present invention can also be rotatable around at least one axis. In another variation, a thin, steel pin was used as a counter electrode and was placed behind a rotating, non-conductive cylindrical collector. The rotating drum can also be combined with the previously mentioned multiple field method.

For tissue engineering purposes it might be important to provide a collector shape which allows electrospinning of a scaffold with defined measurements. For example, in case of bone or skin reconstruction it might be necessary to reconstruct a certain specific part of the tissue with specific measurements. When reconstructing specific tissues, such as whole organs or blood vessels, a specific structure of the scaffold will be necessary to mimic the original extracellular membrane (ECM) of the tissue as good as possible.

In one example of the present invention, the collector is a mandrel which is pivotable-mounted to be rotatable around one axis, in this case the horizontal axis.

By "consisting of" is meant including, and limited to, whatever follows the phrase "consisting of". Thus, the phrase "consisting of" indicates that the listed elements are required or mandatory, and that no other elements may be present.

By "comprising" it is meant including, but not limited to, whatever follows the word "comprising". Thus, use of the term "comprising" indicates that the listed elements are required or mandatory, but that other elements are optional and may or may not be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Method for Cryogenic Electrospinning

The polymer used in this example is poly(D,L-lactide) (PLA, LASIA H100J, $T_g$ 58° C., $T_m$ 165° C.), and the solvent is 1,1,1,3,3,3-hexafluoroisopropanol (HFIP, analytical grade, Merck Singapore).

Cryogenic electrospun scaffolds (CES) are fabricated as follows. PLA is dissolved in HFIP at a concentration of 15 wt./vol. %. The PLA solution is then placed in a 30 ml syringe fitted with a 26 gauge metal needle, which is in contact with the earthed plate. The environmental conditions are controlled with an ambient temperature between 20° C.-28° C. and a relative humidity between 25%-80%. The mandrel is chilled to subzero temperatures. Constant pneumatic pressure is applied to the syringe to sustain a droplet at the needle tip. A voltage between 10 to 35 kV is applied to the mandrel until a stable Taylor cone is formed and a constant polymer jet is ejected towards the collector. Electrospun fibers are deposited while ice crystals simultaneously form on the chilled rotating mandrel. When electrospinning is completed, the fibrous mesh is freeze-dried (Freeze-dryer, Alpha 1-2, Germany) overnight to remove the embedded ice crystals. The scaffold is then oven-dried (Thermoline VORD-460-D, Australia) to remove residual solvent. A schematic presentation of this method is illustrated in FIG. 1.

Effect of Relative Humidity of the Environment on Pore Structure of Cryogenic Electrospun Scaffold The effect of the relative humidity of the environment on the pore structure of cryogenic electrospun scaffold is investigated. The relative humidity of the electrospinning chamber is decreased by introducing dry gaseous nitrogen ($N_2$) into the chamber or is increased by introducing water vapour with a humidifier. Three data points, 25% RH, 40% RH and 55% RH (RH=relative humidity) are collected. The mandrel temperature is maintained at −30° C. and all other parameters are kept constant.

Figure 5:
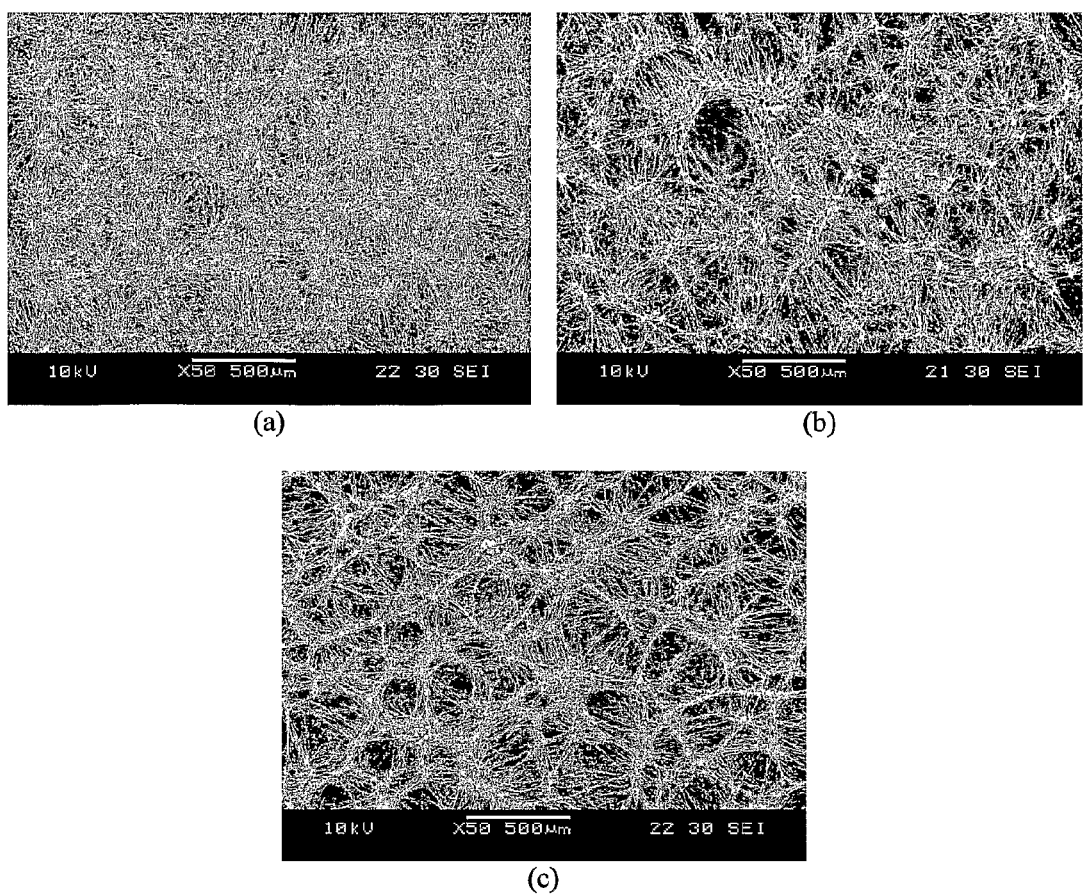
FIG. 5 shows SEM micrographs of the cryogenic electrospun scaffolds collected at different relative humidity of the chamber. (a) 25%, (b) 40% and (c) 55%. It can be observed that as humidity increases from 25% to 55%, the pores of the cryogenic electrospun scaffolds become larger and more defined.

FIG. 5 shows the SEM micrographs for the three data points (FIG. 5a: 25% RH, FIG. 5b: 40% RH and FIG. 5c: 55%). It can be observed that as humidity increases from 25% to 55%, the pores of the cryogenic electrospun scaffolds become larger and more defined. This accord with the observation that simple plate-like structures are formed at low saturations, while higher saturations produce dendritic ice crystals (Libbrecht, K. G., 2005, supra). These complex structures aggregate more readily and occupy more space, resulting in the larger pore size of the cryogenic electrospun scaffold at higher humidities. Moreover, the rate of ice crystal formation increases with humidity; hence the proportion of ice crystals to fiber is increased resulting in a more open structure.

Based on these findings, it can be postulated that parameters that govern ice crystal formation on the mandrel, such as the temperature of the mandrel, temperature and relative humidity of the environment, affects the pore structures of the cryogenic electrospun scaffold. Conditions that favor aggregation and formation of ice crystals result in higher volumes of ice crystals between bundles of electrospun fibers; hence resulting in larger pores of the cryogenic electrospun scaffold.

Effect of Time Interval Between Fiber Deposition on Pore Structure of Cryogenic Electrospun Scaffold Ice crystal formation and fiber deposition are two events that happen simultaneously. It follows that the rates of ice crystal formation and fiber deposition are two competing factors that can affect the pore structure of the cryogenic electrospun scaffolds. To demonstrate the effect of the relative rates of ice crystal formation and fiber deposition on the pore structure of the cryogenic electrospun scaffold, the time interval (X) between fiber deposition is varied. The longer the time interval, the slower the rate of fiber deposition.

The environmental relative humidity (RH) is maintained at 55% RH, and the mandrel temperature is maintained at −30° C. All other parameters are kept constant.

For this study, two waiting periods were used as follows:
(i) Sample A—X=0 minute
(ii) Sample B—X=5 minutes
Samples were labeled as follows:
(i) Sample A: A-5 (spin for 5 mins, X=0), A-10 (spin for 10 mins, X=0), A-15 (spin for 15 mins, X=0)
(ii) Sample B: B-5 (spin for 5 mins, X=5 min), B-10 (spin for 10 mins, X=5 mins), B-15 (spin for 15 mins, X=5 mins)

Figure 6:
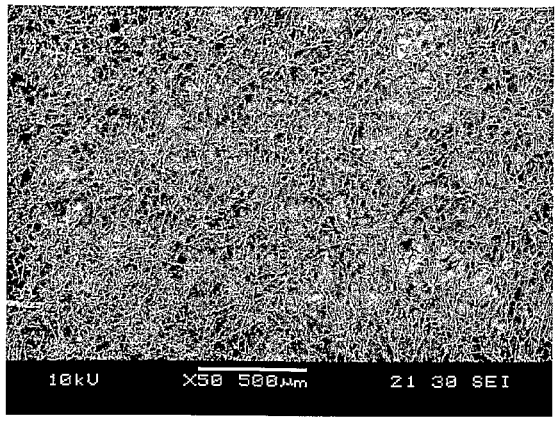
FIGS. 6 (a), (c) and (e) are SEM micrographs showing the pore structures of cryogenic electrospun scaffold after 5, 10 and 15 minutes of spinning without any time interval in between spinning respectively. (b), (d) and (f) are SEM micrographs showing the pore structures of cryogenic electrospun scaffold after 5, 10 and 15 minutes of spinning with a time interval of 5 minutes in between each cycle. From FIG. 6, both Samples A (FIGS. 6 (a), (c) and (e)) & B (FIGS. 6 (b), (d) and (f)) are porous throughout the thickness of the scaffold, as observed by the slow building up over the 5, 10 and 15 minutes. However, pore sizes are smaller in the early stage, becoming bigger as the spinning proceeds. Sample B has pore structures that are larger in diameter and shallower, as compared to Sample A.
Figure 6:
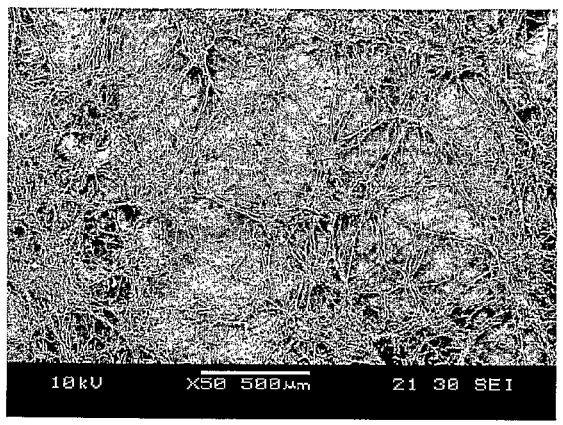
Figure 6:
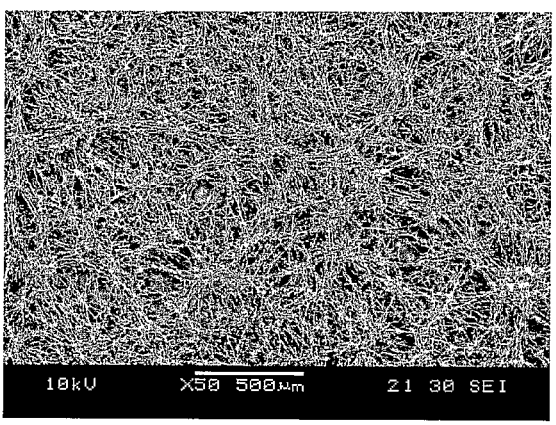
Figure 6:
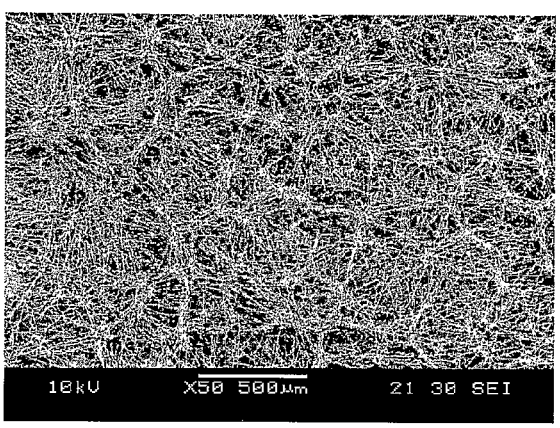
Figure 6:
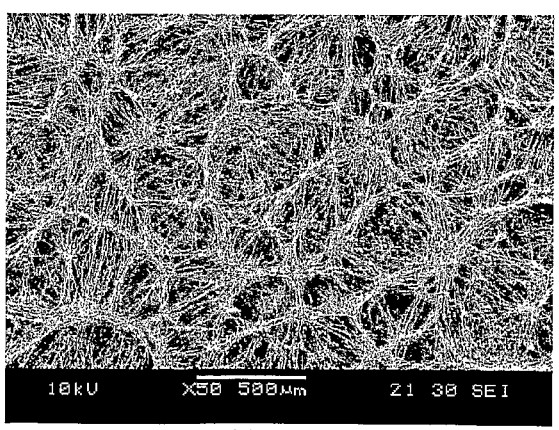
Figure 6:
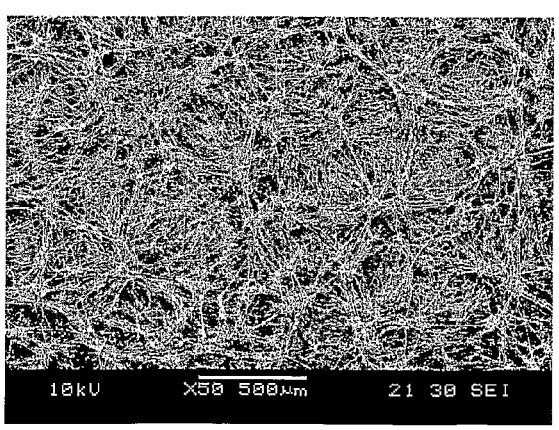

FIG. 6 illustrates the result of this experiment. FIGS. 6 (a), (c) and (e) are SEM micrographs showing the pore structures of cryogenic electrospun scaffold after 5, 10 and 15 minutes of spinning without any time interval in between spinning respectively. FIGS. 6 (b), (d) and (f) are SEM micrographs showing the pore structures of cryogenic electrospun scaffold after 5, 10 and 15 minutes of spinning with a time interval of 5 minutes in between each cycle. From FIG. 6, both Samples A (FIGS. 6 (a), (c) and (e)) & B (FIGS. 6 (b), (d) and (f)) are porous throughout the thickness of the scaffold, as observed by the slow building up over the 5, 10 and 15 minutes. However, pore sizes are smaller in the early stage, becoming bigger as the spinning proceeds. Sample B has pore structures that are larger in diameter and shallower, as compared to Sample A. Both of these observations can be attributed to the time interval X. The waiting period between spinning allows ice crystals to grow in size, hence resulting in larger pores in the cryogenic electrospun scaffold.

Effect of Pore Structures of Cryogenic Electrospun Scaffolds on Cell-Matrix Interactions 3T3/NIH fibroblasts (CRL-1658, ATCC) are used for the in vitro study. Dulbecco's modified Eagle's medium (DMEM) with 4 mM L-glutamine and 4.5 g/l glucose and fetal bovine serum (FBS) are obtained from Hyclone (Logan, Utah, USA). All other reagents are purchased from Sigma-Aldrich Co. and used as received unless otherwise stated.

Oven-dried scaffolds were immersed in 70 vol. % ethanol for 15 minutes. The scaffolds are subsequently rinsed 5 times for 15 minutes with 40 ml of phosphate buffered saline (PBS) per rinse.

The fibroblast are cultured following normal culturing conditions well known in the prior art (Sambrook, et al., Molecular Cloning: A Laboratory Manual, Cold Spring Harbour Lab Publ., 1989, Ausubel, et al., Current Protocols in Molecular Biology, Grene Publishing Associates and Wiley-Interscience, 1987 or Schantz, J.-T., Ng, K. W., A Manual for Primary Human Cell Culture, World Scientific Publishing Company, 2004). The fibroblasts are used for seeding onto each scaffold at a density of $4 \times 10^5$ cells/$cm^2$. The cell-scaffold constructs are kept in culture in DMEM supplemented with 10% FBS and 1% antibiotic-antimycotic solution (AAS) for up to 14 days at 37° C. and 5% $CO_2$. The constructs are cut into 7 μm sections using a microtome (Leica RM2125RT, Germany) and stained with hematoxylin and eosin for analysis.

Figure 7:
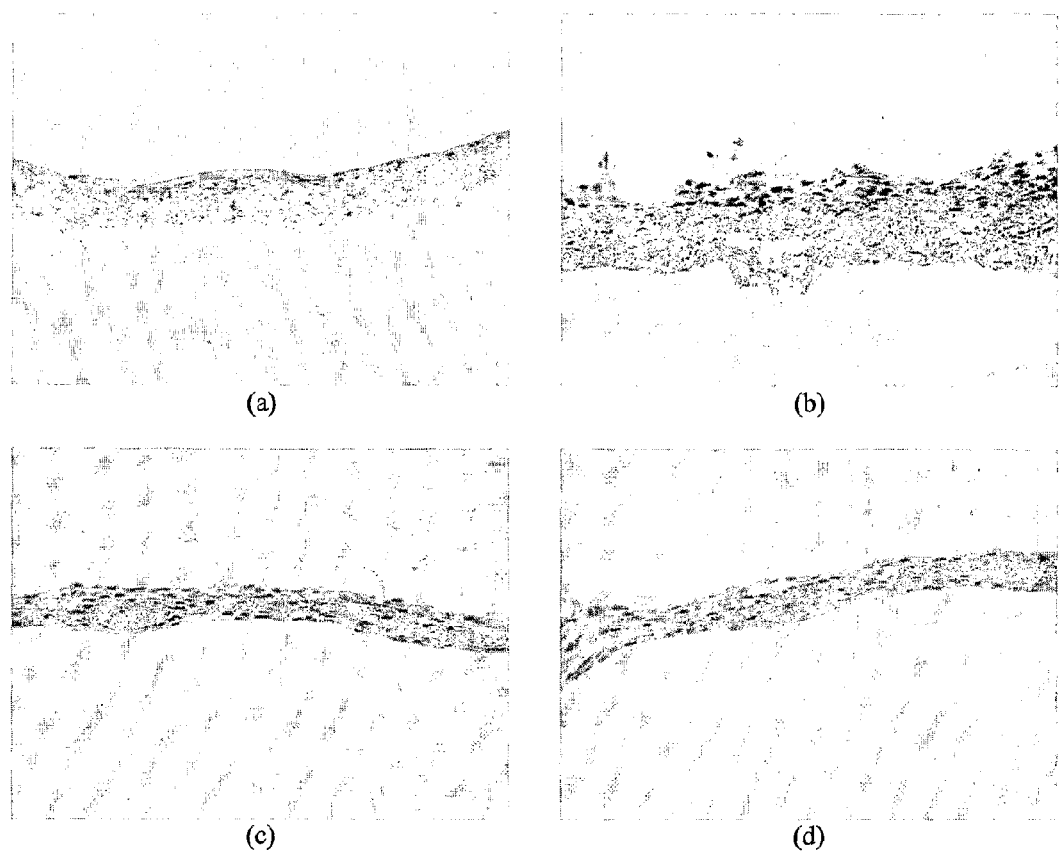
FIG. 7 shows hematoxylin and eosin staining of scaffolds seeded with 3T3/NIH fibroblasts. (a) Conventionally electrospun scaffold at Day 7, (b) conventionally electrospun scaffold at Day 14, (c) CES at Day 7 and (d) CES at Day 14. Hematoxylin and eosin staining shows that fibroblasts cultured on 50 µm thick conventional electrospun scaffold did not infiltrate but proliferated on its surface (FIG. 7(a) and (b)). In contrast, fibroblasts cultured on a cryogenic electrospun scaffold of the same thickness infiltrated the entire cross-section by Day 7 (FIG. 7(c)) and remain attached on Day 14 (FIG. 7(d)) —— represents 50 µm.

The hypothesis that cryogenic electrospun scaffold with its large pores has improved cell infiltration in vitro compared to conventional electrospun scaffolds is tested. This is studied by seeding 3T3/NIH fibroblasts on the surface of both types of scaffold and maintaining the cell-scaffold constructs under static culture conditions for up to two weeks. Hematoxylin and eosin staining shows that fibroblasts cultured on 50 μm thick conventional electrospun scaffold did not infiltrate but proliferated on its surface (FIG. 7(a) and (b)). In contrast, fibroblasts cultured on a cryogenic electrospun scaffold of the same thickness infiltrated the entire cross-section by Day 7 (FIG. 7(c)) and remain attached on Day 14 (FIG. 7(d)). This is attributed to the open structure of the cryogenic electrospun scaffold with its large pores, which present less of an impediment to cell infiltration.

Effect of Pore Structure of Cryogenic Electrospun Scaffolds on In Vivo Cell Infiltration and Vascularization Oven-dried scaffolds are immersed in 70 vol. % ethanol for 15 minutes. The scaffolds were subsequently rinsed 5 times for 15 minutes with 40 ml of phosphate buffered saline (PBS) per rinse.

Wistar rats weighing 300 to 350 g are used for the subcutaneous implantation study. Implantation is performed in an aseptic manner under a laminar hood. The rat is anaesthetized with inhalational isoflurane and oxygen, administered via a facemask. A patch of skin on the dorsum is shaved and cleansed with chlorhexidine and iodine. A single 3 cm dorsal midline incision is made. Three subcutaneous pockets are created by blunt dissection. The cryogenic electrospun scaffolds (CES) and dense conventionally electrospun scaffolds (ES) are inserted into two of the pockets, ensuring that placement is flat and that the scaffolds remained separate from each other. The last pocket is left empty as a negative control for normal healing response. The incision is closed with interrupted 3/0 polypropylene sutures. Postoperatively, an injection of tolfedine 0.1 ml is administered intramuscularly in the thigh for pain relief. Sutures are removed on the tenth postoperative day.

At the specified endpoint (14, 28 and 56 days post implantation), the rat is euthanized by carbon dioxide inhalation. The dorsum is shaved and the previous incision reopened and extended to visualize all three pockets. Each of the scaffolds and the empty pocket are retrieved with the surrounding tissue. The samples are fixed overnight in 10% buffered formalin, embedded in paraffin and 7 µm sections obtained using a microtome (Leica RM2125RT, Germany). These are then stained with hematoxylin and eosin to assess cellular infiltration and vascularization. In addition, sections from the subcutaneous implantation study are also stained with Masson's Trichrome stain to assess tissue capsule and collagen formation. Imaging is performed on a light microscope (Olympus CKX41, Japan).

Figure 9:
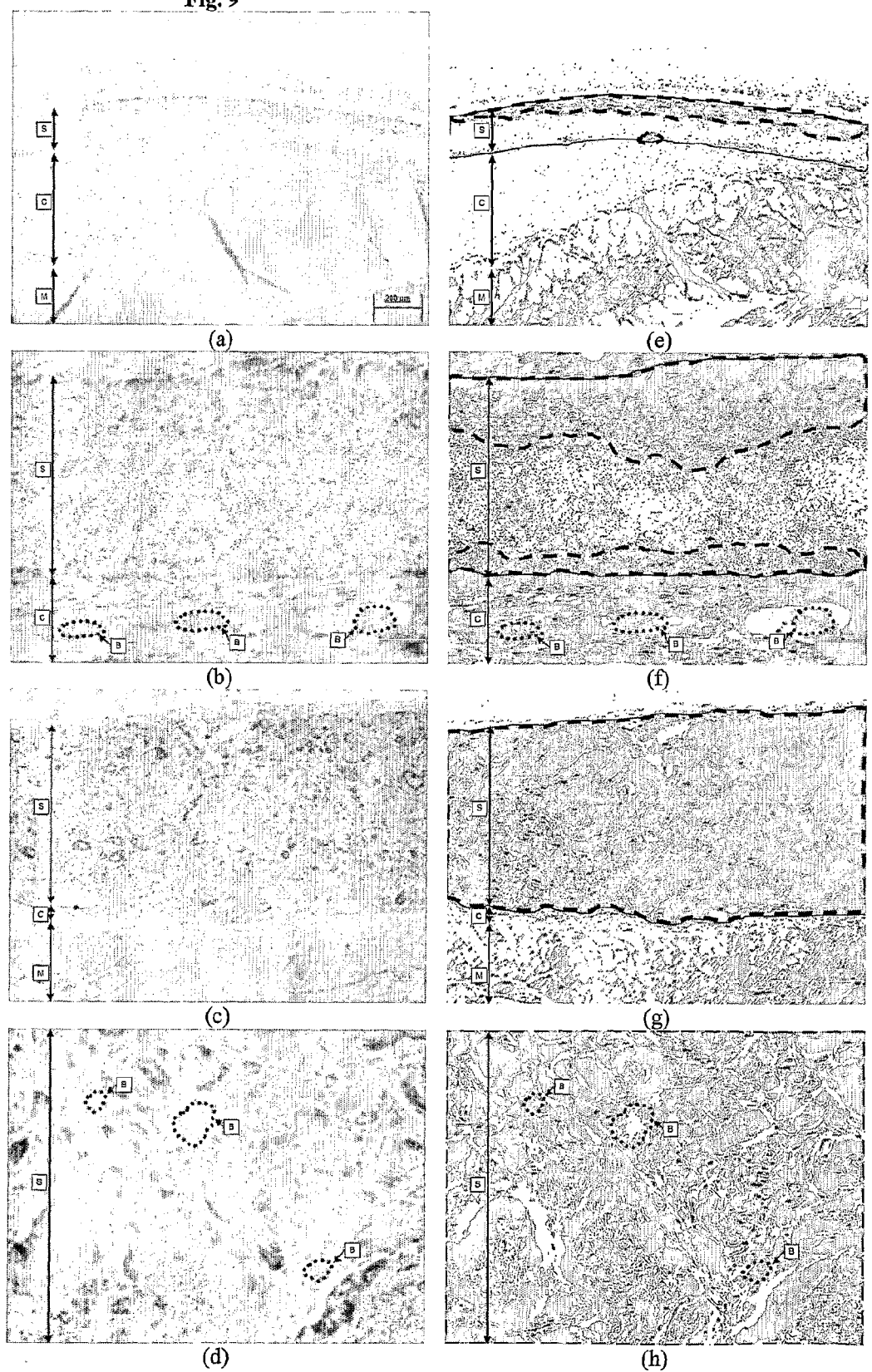
FIG. 9 shows hematoxylin and eosin staining of scaffolds implanted subcutaneously into rats for 28 days. (a) Conventionally electrospun scaffold at 100× magnification, (b) conventionally electrospun scaffold at 400× magnification, (c) CES at 100× magnification and (d) CES at 400× magnification. (S: Scaffold, C: Capsule, M: Underlying muscle, B: Capillaries).
Figure 10:
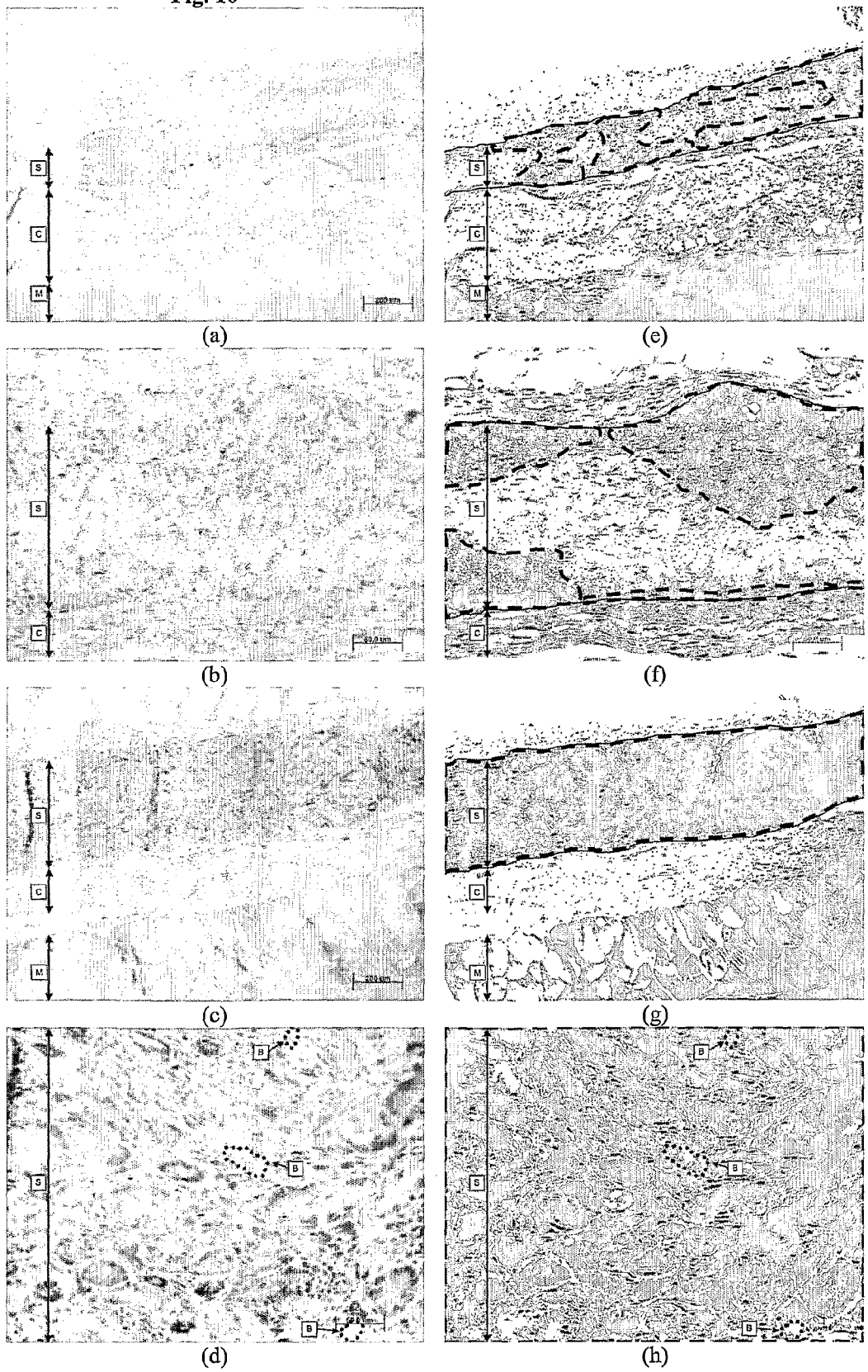
FIG. 10 shows hematoxylin and eosin staining of scaffolds implanted subcutaneously into rats for 56 days. (a) Conventionally electrospun scaffold at 100× magnification, (b) conventionally electrospun scaffold at 400× magnification, (c) CES at 100× magnification and (d) CES at 400× magnification. (S: Scaffold, C: Capsule, M: Underlying muscle, B: Capillaries).
Figure 11:
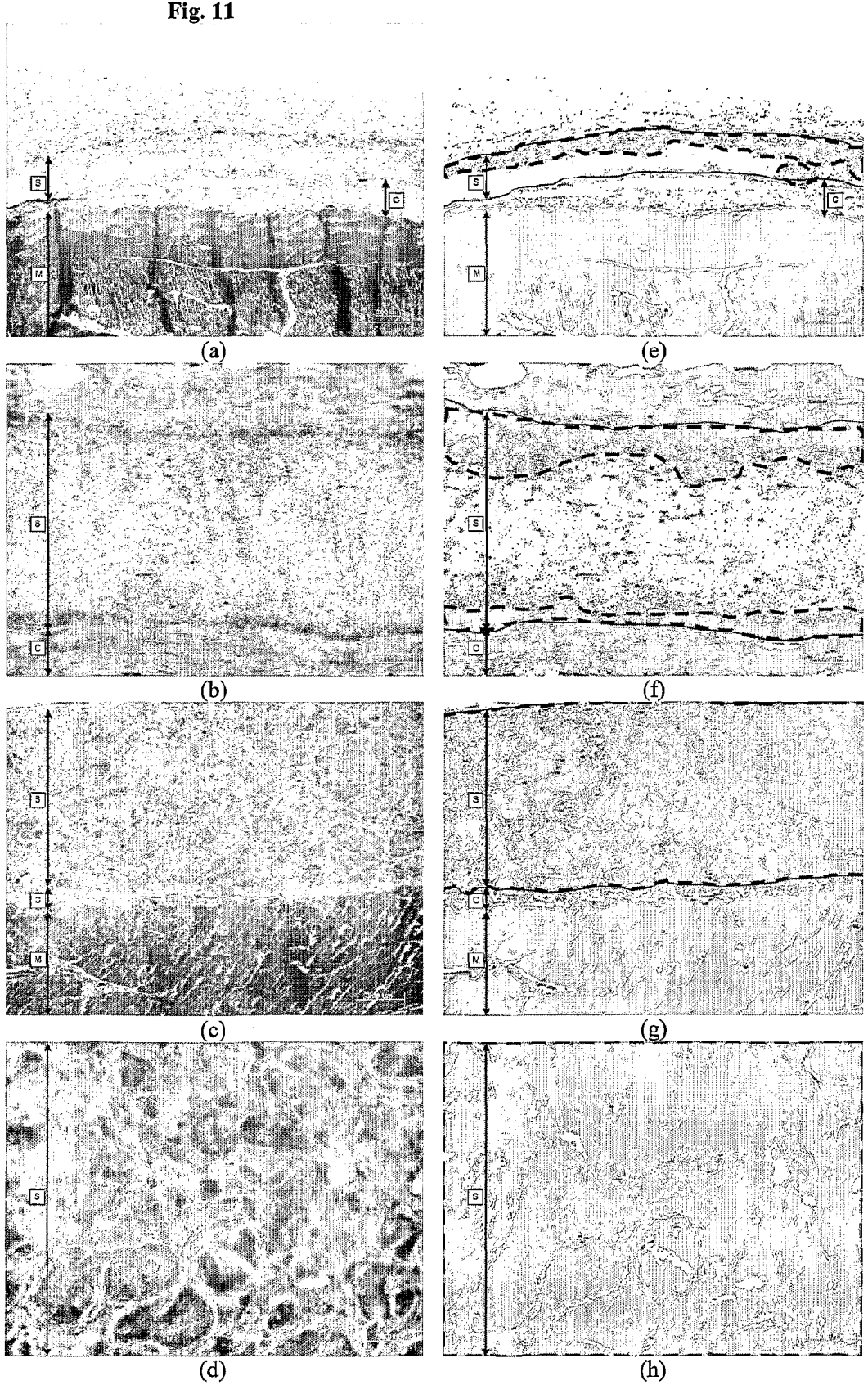
FIG. 11 shows Masson's Trichrome staining of scaffolds implanted subcutaneously for 28 days. (a) Conventionally electrospun scaffold at 100× magnification, (b) conventionally electrospun scaffold at 400× magnification, (c) CES at 100× magnification and (d) CES at 400× magnification. (S: Scaffold, C: Capsule, M: Underlying muscle). There is markedly better cell infiltration in the CES with macrophages and collagen-producing fibroblasts penetrating deep into the scaffold at Day 14 than in the conventional electrospun scaffold, represents 200 µm in (a) and (c) and 50 µm in (b) and (d). Panels e-h of FIG. 11 are grey scale versions of panels a-d of FIG. 11. Regions of the scaffolds infiltrated with cells are circled by the dotted lines.

There is markedly better cell infiltration in the CES with macrophages and collagen-producing fibroblasts penetrating deep into the scaffold at Day 14 (FIGS. 8 and 11) and becoming diffusely infiltrated by 28 days (FIG. 9). In contrast, cells are limited to the periphery of the conventional electrospun scaffold even at 56 days (FIG. 10). The distribution of functional cells within the scaffold indicates that the open structure of the cryogenic electrospun scaffold promotes cell infiltration in vivo.

A second observation is the presence of blood vessels permeating the cryogenic electrospun scaffold as early as Day 14 and persisting on Day 28 and 56 (FIGS. 8(d), 9(d) and 10(d)). The vessels contain intraluminal red blood cells, which imply continuity with the host systemic vasculature. In contrast, blood vessels are absent in conventionally electrospun scaffolds (FIGS. 7(b), 8(b) and 9(b)). This finding may be explained by two mechanisms. The open structure resulting from the large pores of the cryogenic electrospun scaffolds encourage vascular ingrowth, which is known to be optimal at a pore size of 35 to 50 µm (Marshall, A. J. et al., 2004, supra). Also, the abundance of macrophages within the scaffold produces angiogenic growth factors that stimulate vascularisation (Sunderkotter, C., Goebeler, M., et al., 1991, Pharmacology & Therapeutics, vol. 51, p. 195-216). The presence of functional blood vessels that supply cells with oxygen and nutrients and remove waste products allows the fabrication of thick constructs, thus overcoming a major shortcoming of conventional electrospun scaffolds.

It has been shown that the CES promotes cell infiltration and vascularization within thick constructs. Hence, it can be used in applications which require high cell density and the presence of vasculatures such as engineered muscle tissues (Levenberg, S. et al., 2005, supra).

Effect of Mandrel Temperature on the Pore Structure of Cryogenic Electrospun Scaffold The effect of the mandrel temperature on the pore structure of the cryogenic electrospun scaffold is investigated. The temperature of the mandrel which is used in this experiment can be varied by, but not limited to, packing different mass of dry ice inside the hollow mandrel. Three data points (23° C., −15° C., −30° C.) are collected. All other parameters are kept constant.

FIG. 12 shows the SEM micrographs of the cryogenic electrospun scaffolds collected at different mandrel temperatures. For definition purposes it should be mentioned that the "mandrel interface" is the side of the scaffold facing the mandrel and the side of the scaffold facing the air is called the "air interface". It can be observed that a conventional dense electrospun scaffold is obtained when the mandrel temperature is kept at 23° C. When the mandrel temperatures are −15° C. and −30° C., large pore structures (>5 µm) can be observed on both the mandrel and air interfaces of the scaffold. As illustrated in FIG. 1, ice crystals formed on the mandrel at sub-zero temperatures are embedded within the electrospun mesh. The subsequent removal of the ice crystals through freeze-drying forms these pore structures within the electrospun mesh.

In addition, for scaffolds formed at sub-zero temperatures, it can be observed that the mandrel interface of the scaffold have less defined and smaller pore structures as compared to the air interface but still much larger pores than scaffolds obtained using classical electrospinning at room temperature.

The invention claimed is:

1. A method of manufacturing a three-dimensional scaffold using an apparatus for electrospinning comprising a high-voltage power supply; at least one spinneret connected to at least one container comprising a solution with at least one polymer dissolved therein; and a collector, wherein said method comprises:

forming crystals from a molecule or group of molecules in vapor phase comprised in the surrounding atmosphere at the surface of said collector, wherein said collector has a temperature which allows formation of crystals at said surface of said collector;

electrospinning said solution comprising at least one polymer dissolved therein around said crystals;

continuing said formation of crystals and said electrospinning simultaneously; and removing said crystals by sublimation, wherein said crystals are formed from $CO_2$ comprised in said surrounding atmosphere which are removed by sublimation.

2. The method according to claim 1, further comprising increasing or decreasing the temperature of said collector as long as said temperature allows freezing of said molecules or group of molecules from said surrounding atmosphere at said surface of said collector.

3. The method according to claim 1, further comprising increasing or decreasing the temperature around said collector of said electrospinning apparatus.

4. The method according to claim 1, further comprising varying the time interval between said electrospinning and said formation of crystals.

5. The method according to claim 1, further comprising varying at least one of the parameters selected from the group consisting of needle size, voltage, concentration of said at least one polymer in said solution and flow rate of said solution comprising said at least one polymer dissolved therein.

6. The method according to claim 1, wherein said at least one polymer is a biocompatible polymer.

7. The method according to claim 1, wherein said collector is rotatable around at least one axis.

* * * * *